(12) United States Patent
Tang et al.

(10) Patent No.: US 11,235,976 B2
(45) Date of Patent: Feb. 1, 2022

(54) NANOCARBON-IRON COMPOSITE SYSTEM AS WELL AS COMPOSITION, PREPARATION METHOD AND USE THEREOF

(71) Applicant: Chongqing Lummy Pharmaceutical Co., LTD, Chongqing (CN)

(72) Inventors: Xiaohai Tang, Chongqing (CN); Yu Qiu, Chongqing (CN); Yuanfang Huang, Chongqing (CN); Pingfang Xia, Chongqing (CN)

(73) Assignee: SICHUAN YINGRUI PHARMACEUTICAL TECHNOLOGY COMPANY, Chengdu (CN)

( * ) Notice: Subject to any disclaimer, the term of this patent is extended or adjusted under 35 U.S.C. 154(b) by 0 days.

(21) Appl. No.: 16/480,567

(22) PCT Filed: Jan. 26, 2018

(86) PCT No.: PCT/CN2018/074361
§ 371 (c)(1),
(2) Date: Jul. 24, 2019

(87) PCT Pub. No.: WO2018/137708
PCT Pub. Date: Aug. 2, 2018

(65) Prior Publication Data
US 2019/0352183 A1    Nov. 21, 2019

(30) Foreign Application Priority Data
Jan. 26, 2017 (CN) .......................... 201710063374.1

(51) Int. Cl.
| | |
|---|---|
| *C01B 32/174* | (2017.01) |
| *A61P 35/00* | (2006.01) |
| *A61K 9/00* | (2006.01) |
| *A61K 9/10* | (2006.01) |
| *A61K 47/02* | (2006.01) |
| *A61K 47/32* | (2006.01) |
| *B82Y 5/00* | (2011.01) |
| *B82Y 30/00* | (2011.01) |

(52) U.S. Cl.
CPC .......... *C01B 32/174* (2017.08); *A61K 9/0019* (2013.01); *A61K 9/10* (2013.01); *A61K 47/02* (2013.01); *A61K 47/32* (2013.01); *A61P 35/00* (2018.01); *B82Y 5/00* (2013.01); *B82Y 30/00* (2013.01)

(58) Field of Classification Search
CPC .......... A61K 33/26; A61K 33/24; B82Y 5/00
See application file for complete search history.

(56) References Cited

U.S. PATENT DOCUMENTS

| | | | | |
|---|---|---|---|---|
| 6,090,363 | A * | 7/2000 | Green ................... | B82Y 30/00 423/447.1 |
| 2004/0076681 | A1* | 4/2004 | Dennis ................. | A61K 9/0092 424/489 |
| 2015/0093442 | A1* | 4/2015 | Kaneko ................. | A61K 47/32 424/489 |
| 2015/0353519 | A1* | 12/2015 | Tanaka ................... | A61P 25/02 549/402 |

FOREIGN PATENT DOCUMENTS

| | | |
|---|---|---|
| CN | 103183311 | 7/2013 |
| CN | 103213967 | 7/2013 |
| CN | 103359706 | 10/2013 |

OTHER PUBLICATIONS

Dong et al., "Effects of acid treatment on structure, properties and biocompatibility of carbon nanotubes", 2013, Applied Surface Science, vol. 264, pp. 261-268. (Year: 2013).*
Search Report of PCT/CN2018/074361.
Written Opinion of PCT/CN2018/074361.

* cited by examiner

*Primary Examiner* — Michael B. Pallay
(74) *Attorney, Agent, or Firm* — Dragon Sun Law Firm, PC; Jinggao Li, Esq.

(57) ABSTRACT

The present invention provides a nanocarbon-iron composite system which is a composite structure formed by interaction of acid-treated nanocarbon serving as a carrier, with and ferrous ions and/or ferric ions in an iron salt. In an in-vitro experiment and an animal experiment, the nanocarbon-iron composite system of the present invention shows a very efficient inhibition effect on solid tumors containing liver cancer, breast cancer and cervical cancer and has an excellent targeting property. Accordingly, the present invention further provides a preparation method of the nanocarbon-iron composite system, use of the nanocarbon-iron composite system in preparation of a drug for treating solid tumors, and a suspension for injection based on the nanocarbon-iron composite system.

19 Claims, 23 Drawing Sheets

(a1)  (b1)  (c1)  (d1)

(a2)  (b2)  (c2)  (d2)

(a) (b) (c) (d)

NANOCARBON-IRON COMPOSITE SYSTEM AS WELL AS COMPOSITION, PREPARATION METHOD AND USE THEREOF

CROSS-REFERENCE TO RELATED APPLICATIONS

This application is a national stage application of PCT Application No. PCT/CN2018/074361. This Application claims priority from PCT Application No. PCT/CN2018/074361, filed Jan. 28, 2018, and CN Application No. 201710063374.1, filed Jan. 26, 2017, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

TECHNICAL FIELD

The present invention relates to the field of nano drugs, and particularly, to a nanocarbon-iron composite system and a composition and a preparation method thereof as well as use of the nanocarbon-iron composite system in tumor treatment.

BACKGROUND

Cancer is the number one killer that threatens human life at present. 8 million new cases of cancer are diagnosed annually, with 3 million new cases of cancer in China. For solid tumors, a main treatment means at present is surgical resection of cancerous tissues, or chemotherapy to kill cancerous cells, or a combination thereof. Generally, both surgical resection and chemotherapy are relatively effective cancer-treatment procedures. However, there are dilemmas in cancer treatment at present that after surgical resection, tumor cells may metastasize to other parts to cause relapse; and after adoption of chemotherapy, chemotherapeutic drugs attack normal cells and tumor cells without differences, and thus severe toxic and side effects, and even multidrug resistance (MDR) of the tumor cells to chemotherapeutic drugs will be caused.

One method to solve the above dilemmas is cell immunotherapy represented by PD-1, CAR-T and the like, of which the clinical research is developing in full swing around the world and which is expected to be an ultimate solution to conquer certain type of tumors. However, so far it is proved that because of its accuracy at the level of genes, the cell immunotherapy has extraordinary clinical efficacy on some genes, but has no efficacy on other genes. Consequently, it is necessary for global scientists to perform more research and exploration to obtain a more universal tumor treatment scheme.

Besides the cell immunotherapy, in 2012, Dixon et al. discovered a new iron-dependent form of cell apoptosis when researching an action mechanism for killing tumor cells containing mutated oncogenes RAS by small molecule erastin. RAS is the most common oncogene, and RAS protein encoded by RAS is small G protein, whose activity depends on the binding with GTP. The mutated RAS protein loses the activity of hydrolyzing GTP, and thus activates related genes at the downstream of an RAS pathway, leading to cell canceration. RAS-mutated tumor cells can increase the content of iron in cells through up-regulation of a transferrin receptor 1 and down-regulation of ferritin. The use of such a small molecule to treat cells expressing RAS causes cell death through an "oxidative and nonapoptotic" mechanism. Based on lots of research, Dixon et al. appreciated that this cell death form is a new form different from apoptosis, necrosis and autophagy, and named this iron-dependent death form as "ferroptosis" (reference document 1).

Through further research, it was found that the transferrin receptor on the cell surface and the glutamine-fueled intracellular metabolic pathway played crucial roles in the death process. Inhibition of glutamine is an essential part of ferroptosis and can reduce heart damage caused by ischemia reperfusion, which suggests that ferroptosis is a potential method for treating related diseases (reference document 2).

On the basis of the above research, after the action mechanism of "ferroptosis" is confirmed, in 2016, a tumor laboratory in America uses ultrasmall (<10 nm in diameter) polyethylene glycol-coated silica nanoparticles functionalized with melanoma-targeting polypeptides. These silica nanoparticles can induce a form of programmed cell death known as "ferroptosis" in starved cancer cells and tumor-bearing mice. In the further research, through the lipid reactive oxygen species (ROS) assay and experiments using an iron chelator (DFO), it was demonstrated that the silica nanoparticles induce apoptosis by means of ferroptosis (reference document 3).

Furthermore, the review literature *Ferroptosis: process and function* published in the subsidiary journal of Nature in 2016 comprehensively reviewed and summarized research conclusions about ferroptosis since ferroptosis was proposed in 2012. It pointed out that ferroptosis is characterized morphologically in that mitochondria become small, the density of a mitochondrial membrane is increased, a mitochondrial crista is reduced or vanished and an outer mitochondrial membrane ruptures. Ferroptosis can be induced by experimental compounds (e.g., erastin, Ras-selective lethal small molecule 3, and buthionine sulfoximine) or clinical drugs (e.g., sulfasalazine, sorafenib, and artesunate) in cancer cells and certain normal cells (e.g., kidney tubule cells, neurons, fibroblasts, and T cells). Activation of mitochondrial voltage-dependent anion channels and mitogen-activated protein kinases, up-regulation of endoplasmic reticulum stress, and inhibition of cystine/glutamate antiporter are involved in the induction of ferroptosis. This process is characterized by the accumulation of lipid peroxidation products and lethal reactive oxygen species (ROS) derived from iron metabolism and can be inhibited by iron chelators (e.g., deferoxamine and desferrioxamine mesylate) and lipid peroxidation inhibitors (e.g., ferrostatin, liproxstatin, and zileuton).

For generation of ROS in ferroptosis that is directly caused apoptosis, the relatively reasonable explanation at present is that due to an increase of intracellular iron concentration, an intracellular Fenton reaction is promoted and thus ROS with extremely high oxidizability is formed and accumulated in cells to cause apoptosis (reference document 5).

The current research shows that iron is the trace element with the highest content in human bodies, is widely distributed in various organs and tissues of the human bodies, and plays an important role in processes of DNA synthesis, electron transfer, oxygen transport and the like. The phenomenon that iron involves in cell death when brain damage and neurodegenerative diseases occur has long been noted. Iron sedimentation has been found in the brains of patients with Parkinson's disease and alzheimer's disease, and iron chelators may protect models of neurotoxicity caused by 6-hydroxydopamine (6-OHDA), 1-methyl-4-phenyl-1, 2, 3, 6-tetrahydropyridine (MPP+) or β-amyloid (Aβ). As the research on ferroptosis is conducted, it is clear that whether ferroptosis exists in various neurodegenerative diseases, and then ferroptosis of nerve cells is regulated through drugs, thereby controlling the occurrence and development of these nervous system diseases. Under the action of various inducers, induction of ferroptosis to act on cells to cause apoptosis may be a bran-new tumor treatment concept.

In addition, the research also discovered that cell iron can also induce functional selection of macrophages. The macrophage is a cell population with relatively high plasticity and pluripotency, shows an obvious functional difference under the influence of different in-vitro and in-vivo microenvironments and is mainly characterized by transformation of anti-inflammatory subspecific M2 macrophages to pro-inflammatory subspecific M1 macrophages. The co-culture of ferumoxytol and macrophages demonstrated an 11-fold increase in hydrogen peroxide and a 16-fold increase in hydroxyl radicals. This indicates that ferumoxytol enhances the production of ROS by macrophages, which increases cancer cell cytotoxicity. To further determine whether ferumoxytol induces M1 macrophages, macrophages are separated from the co-cultures. It was found that mRNA related to pro-inflammatory M1-type response is increased, M1-related TNFα and CD86 markers are up-regulated significantly, and M2-related CD206 and IL10 markers are significantly decreased. In vivo, ferumoxytol significantly inhibits growth of subcutaneous adenocarcinomas in mice. In addition, intravenous ferumoxytol before intravenous tumor cell prevents liver metastasis. Fluorescence-activated cell sorting (FACS) and histopathology research showed that the observed tumor growth inhibition is accompanied by an increase of pro-inflammatory M1 macrophages in the tumor tissues (reference document 6).

In the research on regulation of functional selection of macrophages by iron, it was found that iron in superparamagnetic iron-oxide nanoparticles (SPION) induces a phenotypic shift of THP1 cell-derived M2 macrophages towards high CD86+ and tumor necrosis factors (TNF-α+). This phenotypic shift of M2 macrophages was accompanied by up-regulated levels of ferritin and cathepsin L in the cells, which is a characteristic mark of M1 macrophages (reference document 7).

Currently, some iron-related drugs that have been approved for market comprise iron sucrose such as Venofer®, ferric sodium gluconate complexes such as Ferrlecit and ferridextran, which are absorbed parenterally by injection for solving the problems of severe iron deficiency, iron-deficiency anemia and enteral iron absorption. These drugs, even newer ferumoxytol and the like all aim to supplement the trace element iron in the bodies of patients with iron deficiency, thereby solving the problem of anemia. Such products directly enter blood through intravenous injection to adjust the content of the iron element in blood of a human body for solving the problem of iron deficiency. However, due to existence of cell transferrin, such iron cannot enter cells to induce ferroptosis.

In addition, regarding some clinical developments of nano-iron, the latest patent application WO2015/007730A1 by German scientists proposes an inhibitor for inhibiting ferroptosis, for example, which is expected to treat the ROS stress neurofunctional disorder disease caused by ferroptosis.

It can be seen therefrom that an iron-containing preparation is of great significance for development of antitumor drugs.

At present, research on tumor treatment is developing towards two directions, One is intelligentization, namely, intelligent identification for normal cells and tumor cells; and the other is reduction of toxic and side effects of antitumor drugs, reduction and even elimination of tolerance, and reduction of the dosage of chemotherapeutic drugs, Years of research has shown that nanoparticles can cross cell membranes and directly enter cell nucleuses to act on tumor cells. The accurate drug administration is achieved by taking nanoparticles, such as graphene, magnetic nanoparticles and carbon nanotubes, as a drug carrier, as disclosed in Chinese patent CN105944110A. In this patent, disclosed is a nanocarbon quantum dot-assisted drug-administration carrier system, in which a targeted nanocarrier is formed through covalent coupling of polyethylene glycol (PEG) which is used as a crosslinking agent, and transferrin (TF) which is used as a targeting molecule.

However, for general targeted nanocarrier drugs, there is a very frustrating problem in preparation and animal experiments: how to increase the carrying amount of the drugs and release the drugs at targets accurately. To achieve targeted drug-administration through nanocarrier drugs, the carrying amount of drugs must be increased firstly, namely, a nanocarrier must be associated with a certain number of drug molecules. Secondly, after the nanocarrier drug enter a body to reach a target location through the nanocarrier, the drug molecules carried by the nanocarrier drop off automatically and reach certain concentration, thereby achieving clinical treatment effects.

In addition, the cells have a mechanism to actively excrete iron, so that it is impossible to produce high enough iron concentration in the cells, and thus ferroptosis and cancer cell death that is induced by the polarization of pro-inflammatory macrophages cannot be caused effectively. Therefore, there is an urgent need to find a suitable targeted drug-loaded nano preparation to cooperate with a Fe preparation of appropriate concentration so as to prepare a drug-loaded system, thereby improving the efficiency of iron entering cells. Thus, the cells reach relatively high iron concentration within a short time to induce ferroptosis and the polarization of pro-inflammatory macrophages. In these two action mechanisms, a main action mechanism to induce cancer cell death is polarization of pro-inflammatory macrophages, which produces a series of inflammatory factors and ROS, thus activates the activity of caspase-3 and finally causes cancer cell death in the form of apoptosis.

Reference document 1: Ferroptosis: An Iron-Dependent Form of Nonapoptotic Cell Death, Cell 149, 1060-1072, May 25, 2012;

Reference document 2: Glutaminolysis and Transferrin Regulate Ferroptosis, Molecular Cell 59, 298-308, Jul. 16, 2015;

Reference document 3: Ultrasmall nanoparticles induce ferroptosis in nutrient-deprived cancer cells and suppress tumor growth, Nature Technology, 26 Sep. 2016;

Reference document 4: Ferroptosis: process and function, Cell Death and Differentiation 23, 369-379, 2016;

Reference document 5: Generation of hydrogenperoxide primarily contributes to the induction of Fe(II)-dependentapoptosis in Jurkat cells by (−)-epigallocatechin gallate, Carcinogenesis, 25(9), 1567-1574, 2004;

Reference document 6: Iron oxide nanoparticles inhibit tumor growth by inducing pro-inflammatory macrophage polarization in tumor tissues, Nature NanoTechnology, Sep. 26, 2016; and Reference document 7: SPION primes THP1 derived M2 macrophages towards M1-like macrophages, Biochemical and Biophysical Research Communications 441, 737-742, 2013.

SUMMARY

Aiming at the problem existing in tumor treatment at present, based on cancer cell apoptosis induced by polarization of M1 macrophages and an accurate administration characteristic of nanoparticles, the present invention proposes a combination system in which nanocarbon carries iron. This combination system shows an excellent inhibition effect on solid tumors in in-vitro cell experiments and animal experiments.

The present invention proposes a nanocarbon-iron composite system.

The composite system is a composite structure which is formed by acid-treated nanocarbon serving as a carrier, and ferrous ions and/or ferric ions in an iron salt. The composite system has a particle size of 50-500 nm, preferably 90-300 nm, more preferably 100-250 nm and still more preferably 120-180 nm.

The composite system as mentioned above is characterized in that the ferrous ions and/or ferric ions in the iron salt have a concentration of 1.36-13.6 mg/mL, preferably 1.5-8.33 mg/mL and more preferably 2.73-5.46 mg/mL.

The composite system as in any of the above is characterized in that the iron salt is selected from any one or more of ferrous sulfate, ferric sulfate, ferrous chloride, ferric chloride, ferrous gluconate, iron sucrose, ammonium ferric citrate, ferrous succinate, iron sorbitol and ferrous fumarate; preferably the iron salt is ferrous sulfate, ferric sulfate, ferrous chloride or ferric trichloride; and more preferably, the iron salt is ferrous sulfate.

The composite system as in any of the above is characterized in that the composite system has a pH of 3.0-6.0 and preferably 3.5-4.5.

The composite system as in any of the above is characterized in that the mass ratio of the nanocarbon to an iron element is 40:1-3:1, preferably 30:1-5:1 and more preferably 18:1-6:1.

The composite system as mentioned above is characterized in that the nanocarbon has a carbon content of 86-98%, a hydrogen content of 0.5-2.5%, and an oxygen content of 1.0-10.0%, and preferably has the carbon content of 94-97%, the hydrogen content of 0.7-1.0%, and the oxygen content of 2.0-4.5%.

The composite system as in any of the above is characterized in that the nanocarbon comprises at least one or more of carbon nanoparticles, carbon nanotubes, carbon quantum dots, graphene, fullerene, carbon nanorods and carbon nanofibres; preferably the nanocarbon is carbon nanoparticles; and more preferably, the nanocarbon is nano-carbon-black $C_{40}$.

The composite system as in any of the above is characterized in that the nanocarbon has a carboxyl content of 0.01-2.0 mmol/g, preferably 0.01-1.0 mmol/g, and more preferably 0.03-0.7 mmol/g.

The composite system as in any of the above is characterized in that the nanocarbon and the iron salt form a composite structure by a combination of various interactions such as electrostatic interaction, complexation and the Van der Waals force.

The composite system as in any of the above is characterized in that the composite system further comprises sodium citrate, wherein the mass ratio of the sodium citrate to the iron element in the iron salt is 0.1-3, and preferably 1-2. Preferably, the sodium citrate and ferrous ions and/or ferric ions form a complex.

The composite system as in any of the above is characterized in that the composite system further comprises a suspending agent, wherein the suspending agent is selected from one or more of methylcellulose, sodium carboxymethylcellulose, hydroxypropyl cellulose, polyvinylpyrrolidone and glucan; and preferably the suspending agent is polyvinylpyrrolidone K30. The suspending agent can increase viscosity of a dispersion medium so as to reduce the sedimentation speed of particles or increase hydrophilic additives of particles.

The suspending agent has a concentration of 10-40 mg/ml and preferably 15-25 mg/ml.

The present invention further proposes a preparation method of the nanocarbon-iron composite system, which is characterized in that method I or method II is adopted for preparation:

method I comprises the following steps:

a) uniformly dispersing acid-treated nanocarbon in a normal saline solution of a suspending agent to prepare a suspension; and then adjusting a pH value of the suspension to 6.5-8.0, preferably 6.8-7.2 with sodium citrate;

b) mixing the nanocarbon suspension obtained in step a) with an iron salt, and performing stirring with exclusion of air until the iron salt is completely dissolved to obtain a mixed solution; and c) homogenizing the mixed solution obtained in step b) with a high-pressure homogenizer to obtain homogenate, and obtaining the composite system when the pH of the homogenate is determined to be 3.0-6.0, and preferably 3.5-4.5, wherein the homogenization pressure is 30-120 MPa and preferably 90 MPa;

or method II is adopted for preparation, which comprises the following steps:

a) uniformly dispersing acid-treated nanocarbon in a normal saline solution of a suspending agent, performing homogenization for 5 minutes to prepare a suspension, and adjusting a pH value of the suspension to 6.5-8.0, preferably 6.8-7.2 with sodium citrate; performing homogenization with a high-pressure homogenizer to obtain a mixed solution and bottling the mixed solution for later use, wherein preferably the homogenization pressure is 30-120 MPa and preferably 90 MPa;

b) dissolving an iron salt into normal saline, performing bottling and freeze-drying, sealing the bottle by filling the bottle with nitrogen for preservation to obtain an iron salt solid; and c) during use, dissolving the solid obtained in step b), then uniformly mixing the dissolved solid with the mixed solution obtained in step a), and obtaining the composite system when the pH of the mixture is determined to be 3.0-6.0, and preferably 3.5-4.5.

The present invention further proposes use of the above nanocarbon-iron composite system in preparation of a drug for treating solid tumors, preferably in preparation of a drug for treating liver cancer, lung cancer, stomach cancer, colon cancer, breast cancer, cervical cancer, thyroid cancer or ovarian cancer, and more preferably in preparation of a drug for treating the breast cancer, the cervical cancer and the liver cancer.

The present invention further provides a suspension for injection, comprising the nanocarbon-iron composite system as in any of the above, wherein the nanocarbon-iron composite system is dispersed uniformly and stably in a mixed solution containing polyvinylpyrrolidone and sodium citrate; preferably the polyvinylpyrrolidone is polyvinylpyrrolidone K30; and preferably, in the composite system, the ferrous irons or/and ferric ions have a concentration of 1.36-13.6 mg/mL, preferably 1.5-8.33 mg/mL and still more preferably 2.73-5.46 mg/m L.

Beneficial Effects

The theoretical analysis, in-vitro cell experiments and animal experiments all show that the nanocarbon-iron composite system proposed in the present invention has the following effects.

1. A stable nanocarbon-iron composite system is formed and the system has excellent stability and biocompatibility.

2. By taking the nanocarbon as the carrier to transfer iron, a better transferring effect is achieved; because the cells themselves have a mechanism to excrete iron, it is impossible to produce a high enough iron concentration in the cells, and then ferroptosis and cancer cell death induced by the polarization of proinflammatory macrophages cannot be caused effectively; and after the nanocarbon is used as the carrier, the efficiency that iron enters cells can be improved, and the cells have a relatively high iron concentration with a short time to produce ferroptosis and induce polarization of macrophages, thereby facilitating cancer cell apoptosis.

3. This preparation has a very strong inhibition effect on all solid tumors including SMMC7721 liver cancer cells, A549 lung cancer cells, SGC-7901 stomach cancer cells, HCT116 colon cancer cells, MDA-MB-231 breast cancer cells, Hela cervical cancer cells, TPC-1 thyroid cancer cells, SKOV3 ovarian cancer cells and murine liver cancer H22 cells, and particularly has a better treatment effect on breast cancer, cervical cancer and liver cancer.

BRIEF DESCRIPTION OF THE DRAWINGS

FIG. 1a is an XPS spectrum of acid-treated nanocarbon;

FIG. 1b is an XPS spectrum of an acid-treated nanocarbon-iron composite system;

FIG. 3a 1 is a diagram showing ferric ions of cells in a negative control group after Prussian-blue staining;

FIG. 3b 1 is a diagram showing ferric ions of cells in a nanocarbon group after Prussian-blue staining;

FIG. 3c 1 is a diagram showing ferric ions of cells in a ferrous sulfate group after Prussian-blue staining;

FIG. 3d 1 is a diagram showing ferric ions of cells in a nanocarbon-ferrous sulfate composite system group after Prussian-blue staining;

FIG. 3a 2 is a diagram showing ferric ions of H22 tumors in a negative control group after Prussian-blue staining;

FIG. 3b 2 is a diagram showing ferric ions of H22 tumors in the nanocarbon group after Prussian-blue staining;

FIG. 3c 2 is a diagram showing ferric ions of H22 tumors in the ferrous sulfate group after Prussian-blue staining;

FIG. 3d 2 is a diagram showing ferric ions of H22 tumors in the nanocarbon-ferrous sulfate composite system group after Prussian-blue staining;

DETAILED DESCRIPTION

I. Preparation of Nanocarbon-iron Composite System

Figure 1:
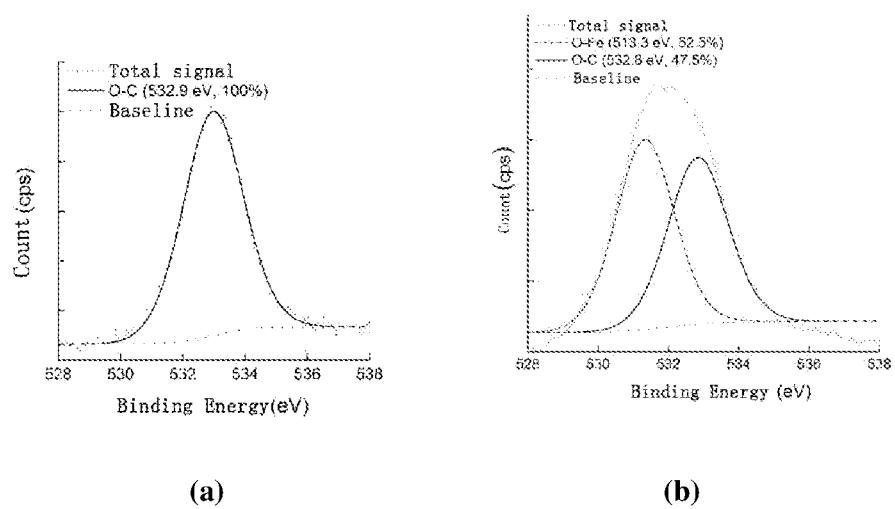

The following samples are prepared and raw material compositions of samples are shown in tables 1-16 below in details, respectively.

1. Nanocarbon+Ferrous Sulfate

TABLE 1

| Number | Nanocarbon Content (mg), Carboxyl Content (mmol/G) and Particle Size (nm) | Ferrous Sulfate Heptahydrate (mg) | PVP (mg) | Normal Saline (ml) | Sodium Citrate | Homogenization Pressure (mpa)/Number of Times |
|---|---|---|---|---|---|---|
| 1A | 250, 0.01, 160 | 135.5 | 200 | 10 | 50 | 90/3 |
| 1B | 500, 0.01, 160 | 271.0 | 200 | 10 | 50 | 90/3 |
| 2A | 250, 0.07, 160 | 135.5 | 200 | 10 | 50 | 90/3 |
| 2B | 500, 0.07, 160 | 271.0 | 200 | 10 | 50 | 90/3 |
| 3A | 250, 2.00, 160 | 135.5 | 200 | 10 | 50 | 90/3 |
| 3B | 500, 2.00, 160 | 271.0 | 200 | 10 | 50 | 90/3 |
| 4A | 200, 0.07, 160 | 67.8 | 200 | 10 | 50 | 90/3 |
| 4B | 400, 0.07, 160 | 135.5 | 200 | 10 | 50 | 90/3 |
| 5A | 400, 0.07, 160 | 271 | 200 | 10 | 50 | 90/3 |
| 5B | 800, 0.07, 160 | 542 | 200 | 10 | 50 | 90/3 |
| 6A | 800, 0.07, 160 | 406.5 | 200 | 10 | 50 | 90/3 |
| 6B | 1600, 0.07, 160 | 813 | 200 | 10 | 50 | 90/3 |
| 7A | 1000, 0.07, 160 | 677.5 | 200 | 10 | 50 | 90/3 |
| 7B | 2000, 0.07, 160 | 1355 | 200 | 10 | 50 | 90/3 |
| 8A | 2500, 0.07, 160 | 1355 | 2000 | 100 | 500 | 90/3 |
| 8B | 5000, 0.07, 160 | 2710 | 2000 | 100 | 500 | 90/3 |
| 9A | 25000, 0.07, 160 | 13550 | 20000 | 1000 | 5000 | 90/3 |
| 9B | 50000, 0.07, 160 | 27100 | 20000 | 1000 | 5000 | 90/3 |
| 10A | 250, 0.07, 160 | 135.5 | 100 | 10 | 50 | 90/3 |
| 10B | 500, 0.07, 160 | 271.0 | 100 | 10 | 50 | 90/3 |
| 11A | 250, 0.07, 160 | 135.5 | 400 | 10 | 50 | 90/3 |
| 11B | 500, 0.07, 160 | 271.0 | 400 | 10 | 50 | 90/3 |
| 12A | 250, 0.07, 90 | 135.5 | 200 | 10 | 50 | 120/5 |
| 12B | 500, 0.07, 90 | 271.0 | 200 | 10 | 50 | 120/5 |

TABLE 1-continued

| Number | Nanocarbon Content (mg), Carboxyl Content (mmol/G) and Particle Size (nm) | Ferrous Sulfate Heptahydrate (mg) | PVP (mg) | Normal Saline (ml) | Sodium Citrate | Homogenization Pressure (mpa)/Number of Times |
|---|---|---|---|---|---|---|
| 13A | 250, 0.07, 120 | 135.5 | 200 | 10 | 50 | 110/3 |
| 13B | 500, 0.07, 120 | 271.0 | 200 | 10 | 50 | 110/3 |
| 14A | 250, 0.07, 180 | 135.5 | 200 | 10 | 50 | 80/3 |
| 14B | 500, 0.07, 180 | 271.0 | 200 | 10 | 50 | 80/3 |
| 15A | 250, 0.07, 300 | 135.5 | 200 | 10 | 50 | 60/3 |
| 15B | 500, 0.07, 300 | 271.0 | 200 | 10 | 50 | 60/3 |
| 16A | 250, 0.07, 500 | 135.5 | 200 | 10 | 50 | 30/2 |
| 16B | 500, 0.07, 500 | 271.0 | 200 | 10 | 50 | 30/2 |

2. Nanocarbon+Ferrous Chloride

TABLE 2

| Number | Nanocarbon Content (mg), Carboxyl Content (mmol/g) and Particle Size (nm) | Ferrous Chloride Tetrahydrate | PVP (mg) | Normal Saline (mL) | Sodium Citrate | Homogenization Pressure (mpa)/Number of Times |
|---|---|---|---|---|---|---|
| 17 | 250, 0.07, 160 | 48.5 | 200 | 10 | 50 | 90/3 |
| 18 | 250, 0.07, 160 | 96.9 | 200 | 10 | 50 | 90/3 |
| 19 | 250, 0.07, 160 | 290.7 | 200 | 10 | 50 | 90/3 |

3. Nanocarbon+Ferric Chloride

TABLE 3

| Number | Nanocarbon Content (mg), Carboxyl Content (mmol/g) and Particle Size (nm) | Ferric Chloride (mg) | PVP (mg) | Normal Saline (mL) | Sodium Citrate | Homogenization Pressure (mpa)/ Number of Times |
|---|---|---|---|---|---|---|
| 22 | 250, 0.07, 160 | 48.5 | 200 | 10 | 50 | 90/3 |
| 23 | 250, 0.07, 160 | 96.9 | 200 | 10 | 50 | 90/3 |
| 24 | 250, 0.07, 160 | 290.7 | 200 | 10 | 50 | 90/3 |

4. Nanocarbon+Ferric Sulfate

TABLE 4

| Number | Nanocarbon Content (mg), Carboxyl Content (mmol/g) and Particle Size (nm) | Ferric Sulfate (mg) | PVP (mg) | Normal Saline (mL) | Sodium Citrate | Homogenization Pressure (mpa)/ Number of Times |
|---|---|---|---|---|---|---|
| 25 | 250, 0.07, 160 | 48.7 | 200 | 10 | 50 | 90/3 |
| 26 | 250, 0.07, 160 | 97.5 | 200 | 10 | 50 | 90/3 |
| 27 | 250, 0.07, 160 | 292.5 | 200 | 10 | 50 | 90/3 |

5. Carbon Nanotube+Ferrous Sulfate Heptahydrate

TABLE 5

| Number | Carbon Nanotube Content (mg), Carboxyl Content (mmol/g) and Particle Size (nm) | Ferrous Sulfate Heptahydrate (mg) | PVP (mg) | Normal Saline (mL) | Sodium Citrate | Homogenization Pressure (mpa)/ Number of Times |
|---|---|---|---|---|---|---|
| 28 | 250, 0.07, 160 | 135.5 | 200 | 10 | 50 | 90/3 |

6. Graphene+Ferrous Sulfate Heptahydrate

TABLE 6

| Number | Graphene content (mg), Carboxyl Content (mmol/g) and Particle Size (nm) | Ferrous Sulfate Heptahydrate (mg) | PVP (mg) | Normal Saline (mL) | Sodium Citrate | Homogenization Pressure (mpa)/ Number of Times |
|---|---|---|---|---|---|---|
| 29 | 250, 0.07, 160 | 135.5 | 200 | 10 | 50 | 90/3 |

7. Carbon Quantum Dots+Ferrous Sulfate Heptahydrate

TABLE 7

| Number | Carbon Quantum Dot Content (mg), Carboxyl Content (mmol/g) and Particle Size (nm) | Ferrous Sulfate Heptahydrate (mg) | PVP (mg) | Normal Saline (mL) | Sodium Citrate | Homogenization Pressure (mpa)/Number of Times |
|---|---|---|---|---|---|---|
| 30 | 250, 0.07, 160 | 135.5 | 200 | 10 | 50 | 90/3 |

8. Fullerene+Ferrous Sulfate Heptahydrate

TABLE 8

| Number | Fullerene Content (mg), Carboxyl Content (mmol/g) and Particle Size (nm) | Ferrous Sulfate Heptahydrate (mg) | PVP (mg) | Normal Saline (mL) | Sodium Citrate | Homogenization Pressure (mpa)/Number of Times |
|---|---|---|---|---|---|---|
| 31 | 250, 0.07, 160 | 135.5 | 200 | 10 | 50 | 90/3 |

9. Activated Carbon+Ferrous Sulfate Heptahydrate

TABLE 9

| Number | Activated Carbon Content (mg), Carboxyl Content (mmol/g) and Particle Size (nm) | Ferrous Sulfate Heptahydrate (mg) | PVP (mg) | Normal Saline (mL) | Sodium Citrate | Homogenization Pressure (mpa)/Number of Times |
|---|---|---|---|---|---|---|
| 32 | 250, 0.07, 160 | 135.5 | 200 | 10 | 50 | 90/3 |

10. Nanocarbon+Ferric Hydroxide

TABLE 10

| Number | Activated Carbon Content (mg), Carboxyl Content (mmol/g) and Particle Size (nm) | Ferric Hydroxide (mg) | PVP (mg) | Normal Saline (mL) | Sodium Citrate | Homogenization Pressure (mpa)/Number of Times |
|---|---|---|---|---|---|---|
| 33 | 500, 0.07, 160 | 25.9 | 200 | 10 | 50 | 90/3 |
| 34 | 500, 0.07, 160 | 51.9 | 200 | 10 | 50 | 90/3 |
| 35 | 500, 0.07, 160 | 155.7 | 200 | 10 | 50 | 90/3 |

11. Nanocarbon+Iron Sucrose

TABLE 11

| Number | Nanocarbon Content (mg), Carboxyl Content (mmol/g) and Particle Size (nm) | Commercially-Available Iron Sucrose (ml) | PVP (mg) | Normal Saline (mL) | Sodium Citrate | Homogenization Pressure (mpa)/Number of Times |
|---|---|---|---|---|---|---|
| 36 | 250, 0.07, 160 | 0.7 | 200 | 9.3 | 50 | 90/3 |
| 37 | 250, 0.07, 160 | 1.4 | 200 | 8.6 | 50 | 90/3 |
| 38 | 250, 0.07, 160 | 4.2 | 200 | 5.8 | 50 | 90/3 |

12. Nanocarbon+Ferrous Succinate

TABLE 12

| Number | Nanocarbon Content (mg), Carboxyl Content (mmol/g) and Particle Size (nm) | Commercially-Available Ferrous Succinate (ml) | PVP (mg) | Normal Saline (mL) | Sodium Citrate | Homogenization Pressure (mpa)/Number of Times |
|---|---|---|---|---|---|---|
| 39 | 250, 0.07, 160 | 0.25 | 200 | 9.7 | 50 | 90/3 |
| 40 | 250, 0.07, 160 | 0.5 | 200 | 9.5 | 50 | 90/3 |
| 41 | 250, 0.07, 160 | 1.5 | 200 | 8.5 | 50 | 90/3 |

13. Nanocarbon+Ferrous Gluconate

TABLE 13

| Number | Nanocarbon Content (mg), Carboxyl Content (mmol/g) and Particle Size (nm) | Ferrous Gluconate (mg) | PVP (mg) | Normal Saline (mL) | Sodium Citrate | Homogenization Pressure (mpa)/Number of Times |
|---|---|---|---|---|---|---|
| 42 | 250, 0.07, 160 | 108.7 | 200 | 10 | 50 | 90/3 |
| 43 | 250, 0.07, 160 | 217.5 | 200 | 10 | 50 | 90/3 |
| 44 | 250, 0.07, 160 | 652.5 | 200 | 10 | 50 | 90/3 |

14. Nanocarbon+Iron Sorbitol

TABLE 14

| Number | Nanocarbon Content (mg), Carboxyl Content (mmol/g) and Particle Size (nm) | Iron Sorbitol (ml) | PVP (mg) | Normal Saline (mL) | Sodium Citrate | Homogenization Pressure (mpa)/Number of Times |
|---|---|---|---|---|---|---|
| 45 | 250, 0.07, 160 | 0.55 | 200 | 9.4 | 50 | 90/3 |
| 46 | 250, 0.07, 160 | 1.1 | 200 | 8.9 | 50 | 90/3 |
| 47 | 250, 0.07, 160 | 3.3 | 200 | 6.7 | 50 | 90/3 |

15. Nanocarbon+Ferrous Fumarate

TABLE 15

| Number | Nanocarbon Content (mg), Carboxyl Content (mmol/g) and Particle Size (nm) | Ferrous Fumarate (mg) | PVP (mg) | Normal Saline (mL) | Sodium Citrate | Homogenization Pressure (mpa)/Number of Times |
|---|---|---|---|---|---|---|
| 48 | 250, 0.07, 160 | 41.4 | 200 | 10 | 50 | 90/3 |
| 49 | 250, 0.07, 160 | 82.8 | 200 | 10 | 50 | 90/3 |
| 50 | 250, 0.07, 160 | 248.4 | 200 | 10 | 50 | 90/3 |

16. Nanocarbon+Ammonium Ferric Citrate

TABLE 16

| Number | Canocarbon content (mg), Carboxyl Content (mmol/g) and Particle Size (nm) | Ammonium Ferric Citrate (mg) | PVP (mg) | Normal Saline (mL) | Sodium Citrate | Homogenization Pressure (mpa)/Number of Times |
|---|---|---|---|---|---|---|
| 51 | 250, 0.07, 160 | 118.9 | 200 | 10 | 50 | 90/3 |
| 52 | 250, 0.07, 160 | 237.9 | 200 | 10 | 50 | 90/3 |
| 53 | 250, 0.07, 160 | 713.7 | 200 | 10 | 50 | 90/3 |

The specific preparation process of each sample is as follows (samples A are prepared according to method 1 and samples B are prepared according to method 2).

1. Nanocarbon+ferrous sulfate

Sample 1A 200 mg of PVP K30 is added to 10 ml of normal saline; after complete dissolution at the room temperature, 250 mg of nanocarbon powder (carboxyl content: 0.01 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 1B 200 mg of PVP K30 is added to 10 ml of normal saline; after complete dissolution at the room temperature, 500 mg of nanocarbon powder (carboxyl content: 0.01 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 2A 200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 2B 200 mg of PVP K30 is added to 10 ml of normal saline; after complete dissolution at the room temperature, 500 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 3A 200 mg of PVP K30 is added to 10 ml of normal saline; after complete dissolution at the room temperature, 250 mg of nanocarbon powder (carboxyl content: 2.00 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 3B 200 mg of PVP K30 is added to 10 ml of normal saline; after complete dissolution at the room temperature, 500 mg of nanocarbon powder (carboxyl content: 2.00 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 4A 200 mg of PVP K30 is added to 10 ml of normal saline; after complete dissolution at the room temperature, 200 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 67.8 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 4B 200 mg of PVP K30 is added to 10 ml of normal saline; after complete dissolution at the room temperature, 400 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 135.5 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 5A 200 mg of PVP K30 is added to 10 ml of normal saline; after complete dissolution at the room temperature, 400 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 271.0 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 5B 200 mg of PVP K30 is added to 10 ml of normal saline; after complete dissolution at the room temperature, 800 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 542.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 6A 200 mg of PVP K30 is added to 10 ml of normal saline; after complete dissolution at the room temperature, 800 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 406.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 6B 200 mg of PVP K30 is added to 10 ml of normal saline; after complete dissolution at the room temperature, 1600 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 813.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 7A 200 mg of PVP K30 is added to 10 ml of normal saline; after complete dissolution at the room temperature, 1000 mg of nanocarbon powder (carboxyl content: 0.07 mmol/g, and particle size: 160 nm); complete stirring and uniform dispersion are performed, and sodium citrate is added to adjust the pH value to 6.8-7.2 (about 50 mg of sodium citrate is added); 677.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 7B 200 mg of PVP K30 is added to 10 ml of normal saline; after complete dissolution at the room temperature, 2000 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 1355.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 8A 2000 mg of PVP K30 is added to 100 ml of normal saline; after complete dissolution at the room temperature, 2500 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 500 mg of sodium citrate is added); 1355 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 8B 2000 mg of PVP K30 is added to 100 ml of normal saline; after complete dissolution at the room temperature, 5000 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 2710 mg of ferrous sulfate heptahydrate solid is dissolved in 1000 ml of normal saline, bottling and freeze-drying are performed, and the bottle is sealed by filling the bottle with nitrogen for preservation (component II); and component I and component II are mixed during use.

Sample 9A 20000 mg of PVP K30 is added to 1000 ml of normal saline; after complete dissolution at the room temperature, 25000 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 5000 mg of sodium citrate is added); 13550 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 9B 20000 mg of PVP K30 is added to 1000 ml of normal saline; after complete dissolution at the room temperature, 500 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 27100 mg of ferrous sulfate heptahydrate solid is dissolved in 10000 ml of normal saline, bottling and freeze-drying are performed, and the bottle is sealed by filling the bottle with nitrogen for preservation (component II); and component I and component II are mixed during use.

Sample 10A 100 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 10B 100 mg of PVP K30 is added to 10 ml of normal saline; after complete dissolution at the room temperature, 500 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 11A 400 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 11B 400 mg of PVP K30 is added to 10 ml of normal saline; after complete dissolution at the room temperature, 500 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 12A 200 mg of PVP K30 is added to 10 ml of normal saline; after complete dissolution at the room temperature, 250 mg of nanocarbon powder (carboxyl content: 0.07 mmol/g, and particle size: 90 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 5 times (pressure: 120 mpa); a suspension is collected into a penicillin bottle after completion of homogenization; and the penicillin bottle is sealed by filling the penicillin bottle with nitrogen for preservation.

Sample 12B 200 mg of PVP K30 is added to 10 ml of normal saline; after complete dissolution at the room temperature, 500 mg of nanocarbon powder (carboxyl content: 0.07 mmol/g, and particle size: 90 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 5 times (pressure: 120 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 13A 200 mg of PVP K30 is added to 10 ml of normal saline: after complete dissolution at the room temperature, 250 mg of nanocarbon powder (carboxyl content: 0.07 mmol/g, and particle size: 120 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 110 mpa); a suspension is collected into a penicillin bottle after completion of homogenization; and the penicillin bottle is sealed by filling the penicillin bottle with nitrogen for preservation.

Sample 13B 200 mg of PVP K30 is added to 10 ml of normal saline; after complete dissolution at the room temperature, 500 mg of nanocarbon powder (carboxyl content: 0.07 mmol/g, and particle size: 120 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 110 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 14A 200 mg of PVP K30 is added to 10 ml of normal saline; after complete dissolution at the room temperature, 250 mg of nanocarbon powder (carboxyl content: 0.07 mmol/g, and particle size: 180 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 80 mpa); a suspension is collected into a penicillin bottle after completion of homogenization; and the penicillin bottle is sealed by filling the penicillin bottle with nitrogen for preservation.

Sample 14B 200 mg of PVP K30 is added to 10 ml of normal saline; after complete dissolution at the room temperature, 500 mg of nanocarbon powder (carboxyl content: 0.07 mmol/g, and particle size: 180 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 80 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 15A 200 mg of PVP K30 is added to 10 ml of normal saline; after complete dissolution at the room temperature, 250 mg of nanocarbon powder (carboxyl content: 0.07 mmol/g, and particle size: 300 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 60 mpa); a suspension is collected into a penicillin bottle after completion of homogenization; and the penicillin bottle is sealed by filling the penicillin bottle with nitrogen for preservation.

Sample 15B 200 mg of PVP K30 is added to 10 ml of normal saline; after complete dissolution at the room temperature, 500 mg of nanocarbon powder (carboxyl content: 0.07 mmol/g, and particle size: 300 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed 3 times (pressure: 60 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

Sample 16A 200 mg of PVP K30 is added to 10 ml of normal saline; after complete dissolution at the room temperature, 250 mg of nanocarbon powder (carboxyl content: 0.07 mmol/g, and particle size: 500 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed twice (pressure: 30 mpa); a suspension is collected into a penicillin bottle after completion of homogenization; and the penicillin bottle is sealed by filling the penicillin bottle with nitrogen for preservation.

Sample 16B 200 mg of PVP K30 is added to 10 ml of normal saline; after complete dissolution at the room temperature, 500 mg of nanocarbon powder (carboxyl content: 0.07 mmol/g, and particle size: 500 nm) is added; complete stirring and uniform dispersion are performed, and sodium citrate is added to adjust the pH value to 6.8-7.2 (about 50 mg of sodium citrate is added); after complete and uniform mixing at the room temperature, high-pressure homogenization is performed twice (pressure: 30 mpa); a suspension is collected into a penicillin bottle after completion of homogenization; and the penicillin bottle is sealed by filling the penicillin bottle with nitrogen for preservation (component I); 271.0 mg of ferrous sulfate heptahydrate solid is dissolved in 10 ml of normal saline, bottling and freeze-drying are performed, and the bottle is sealed by filling the bottle with nitrogen for preservation (component II); and component I and component II are mixed during use.

2. Nanocarbon+Ferrous Chloride

Sample 17

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 48.5 mg of ferrous chloride is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 18

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 96.9 mg of ferrous chloride is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 19

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 290.7 mg of ferrous chloride is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

3. Nanocarbon+Ferric Chloride

Sample 20

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 65.9 mg of ferric chloride is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 21

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 131.8 mg of ferric chloride is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 22

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 395.4 mg of ferric chloride is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

4. Nanocarbon Ferric Sulfate

Sample 23

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 48.7 mg of ferrous sulfate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 24

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 97.5 mg of ferrous sulfate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 25

200 mg of PVP K30 is added to 10 ml of normal saline; after complete dissolution at the room temperature, 250 mg of nanocarbon powder (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 292.5 mg of ferric sulfate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

5. Carbon Nanotubes+Ferrous Sulfate Heptahydrate

Sample 26

200 mg of PVP K30 is added to 10 ml of normal saline; after complete dissolution at the room temperature, 250 mg of carbon nanotubes (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

6. Graphene+Ferrous Sulfate Heptahydrate

Sample 27

200 mg of PVP K30 is added to 10 ml of normal saline; after complete dissolution at the room temperature, 250 mg of graphene (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

7. Carbon Quantum Dots+Ferrous Sulfate Heptahydrate

Sample 28

200 mg of PVP K30 is added to 10 ml of normal saline; after complete dissolution at the room temperature, 250 mg of carbon quantum dots (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

8. Fullerene+Ferrous Sulfate Heptahydrate

Sample 29

200 mg of PVP K30 is added to 10 ml of normal saline; after complete dissolution at the room temperature, 250 mg of fullerene (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

9. Activated Carbon+Ferrous Sulfate Heptahydrate

Sample 30

200 mg of PVP K30 is added to 10 ml of normal saline; after complete dissolution at the room temperature, 250 mg of activated carbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 135.5 mg of ferrous sulfate heptahydrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

10. Nanocarbon+Ferric Hydroxide

Sample 31

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 51.9 mg of ferric hydroxide is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 32

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 155.7 mg of ferric hydroxide is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

11. Nanocarbon+Iron Sucrose

Sample 33

200 mg of PVP K30 is added to 9.3 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 0.7 mL of iron sucrose is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 34

200 mg of PVP K30 is added to 8.6 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 1.4 mL of iron sucrose is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 35

200 mg of PVP K30 is added to 5.8 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 4.2 mL of iron sucrose is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

12. Nanocarbon+Ferrous Succinate

Sample 36

200 mg of PVP K30 is added to 9.75 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 0.25 mL of ferrous succinate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 37

200 mg of PVP K30 is added to 9.5 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 0.5 mL of ferrous succinate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 38

200 mg of PVP K30 is added to 8.5 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 1.5 mL of ferrous succinate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

13. Nanocarbon+Ferrous Gluconate

Sample 39

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 108.7 mg of ferrous gluconate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 40

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 217.5 mg of ferrous gluconate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 41

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 652.5 mg of ferrous gluconate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

14. Nanocarbon+Iron Sorbitol

Sample 42

200 mg of PVP K30 is added to 9.45 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 0.55 mL of iron sorbitol is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 43

200 mg of PVP K30 is added to 8.9 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 1.1 mL of iron sorbitol is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 44

200 mg of PVP K30 is added to 6.7 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 3.3 mL of iron sorbitol is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

15. Nanocarbon+Ferrous Fumarate

Sample 45

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 41.4 mg of ferrous fumarate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 46

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 82.8 mg of ferrous fumarate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 47

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 248.4 mg of ferrous fumarate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

16. Nanocarbon+Ammonium Ferric Citrate

Sample 48

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 118.9 mg of ammonium ferric citrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 49

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 237.9 mg of ammonium ferric citrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

Sample 50

200 mg of PVP K30 is added to 10 ml of normal saline; after complete dissolution at the room temperature, 250 mg of nanocarbon (carboxyl content: 0.07 mmol/g, and particle size: 160 nm) is added; complete stirring and uniform dispersion are performed, and sodium citrate is added to adjust the pH value to 6.8-7.2 (about 50 mg of sodium citrate is added); 713.7 mg of ammonium ferric citrate is added; after complete and uniform mixing at the room temperature, high-pressure homogenization is performed 3 times (pressure: 90 mpa); a suspension is collected into a penicillin bottle after completion of homogenization; and the penicillin bottle is sealed by filling the penicillin bottle with nitrogen for preservation.

The above samples are prepared from combinations of different raw materials and different iron salts respectively through a similar process. Through the research on the structures and compositions of the nanocarbon-iron composite systems by XPS spectra and infrared spectra, respectively, it was found that the nanocarbon-iron composite systems have a fairly-consistent structure. Therefore, a variety of iron salts can implement the present invention and will not be enumerated here.

As shown in FIG. 1, by comparing the XPS spectra of nanocarbon and the composite system, it can be seen that the addition of Fe causes a new peak of O in nanocarbon, which indicates that Fe interacts with O which accounts for 52.5% in nanocarbon. In conjunction with element composition, the result shows that a plurality of O atoms interacts with the same Fe atom. In the nanocarbon, O mainly exists in the form of C—O single bond (C—OH or C—O—C); and it is difficult to completely ionize C—O—C into C—O—, and only —OH may be partially ionized into —O—. Therefore, the interaction between Fe and O comprises both electrostatic interaction ($Fe^{2+}/Fe^{3+}$ and —O—), and complexation between Fe and O, and is multi-coordination interaction.

It can be seen from the element analysis spectrum that, as shown in table 17, after nanocarbon adsorbs iron, there is less influence on the composition, and a small amount of water coordinates on Fe possibly because Fe is adsorbed on the surface of the nanocarbon, resulting in a slight increase in O content.

TABLE 17

Comparison between element contents of nanocarbon and nanocarbon-iron composite

| Composition | C (at %) | O (at %) | Fe (at %) | N (at %) |
|---|---|---|---|---|
| Nanocarbon | 94.85 | 4.01 | — | 1.15 |
| Nanocarbon-Iron Composite | 92.06 | 6.06 | 0.89 | 1.24 |

Figure 2:
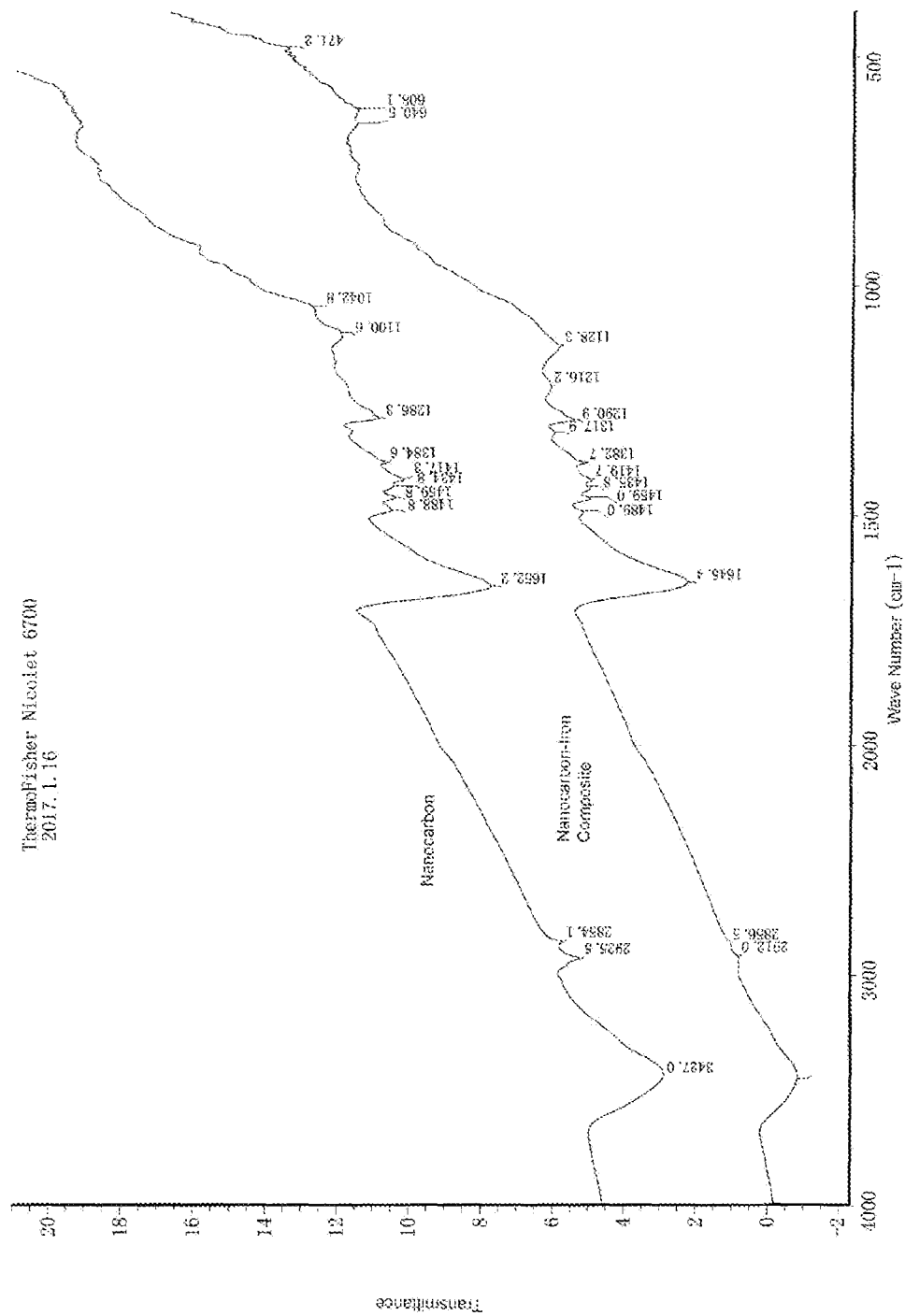
FIG. 2 is an infrared spectrogram of nanocarbon and the nanocarbon-iron composite system.

As shown in the infrared spectra in FIG. 2, the nanocarbon-iron composite has peaks at 1216 $cm^{-1}$, 1128 $cm^{-1}$, 640 $cm^{-1}$, 608 $cm^{-1}$ and 471 $cm^{-1}$ while nanocarbon does not have. Generally, there are new absorption peaks at 604 $cm^{-1}$ and 443 $cm^{-1}$, which indicates that a Fe—O bond exists (absorption peaks of a ferric citrate complex appear at 1216 $cm^{-1}$ and 1128 $cm^{-1}$).

By summarizing results of XPS, element analysis and the infrared spectrum analysis, it can be determined that the nanocarbon-iron composite is a composite formed by a combination of various interactions such as electrostatic interaction, complexation and Van der Waals force.

For selection of the particle size and concentration, the nanocarbon used in an experiment is such nanocarbon that contains certain amount (0.01-0.10 mmol/g) of carboxyl on the surface after acid oxidation treatment. When the carboxyl content is lower than 0.03 mmol/g, the stability of a suspension system is reduced and deposition occurs easily. Thus, it is impossible to form a stable suspension. Since carboxyl is a hydrophilic group, the higher content of carboxyl facilitates the stability of the suspension system. Although an increase in the content of polyvinylpyrrolidone K30 (PVP K30) can also improve the stability of the suspension system to some extent, it also significantly increases the viscosity of the system, which is unfavourable for injection administration. When the carboxyl content is higher than 0.08 mmol/g, the colour of the suspension becomes light (change from black to light black), which is unfavourable for observation on nanocarbon tracing effects. Therefore, considering comprehensively, it is reasonable that the content range of carboxyl is 0.03-0.08 mmol/g.

For the nanocarbon-iron composite system, a preparation has requirements for the particle size of the suspension in the aspects of both the stability and pharmacological efficacy. Since the blood capillary of a tumor tissue has a hole diameter of about 50 nm and a lymphatic vessel has a hole diameter of about 150 nm, when the nanocarbon-iron composite has a particle size of less than 50 nm, it is easy to enter the blood capillary, affecting the concentration of iron in blood. In addition, macrophages selectively phagocytose particles, and the larger the particle size is, the easier it is to be phagocytosed by macrophages. When the nanocarbon has the particle size of greater than 300 nm, the stability of the suspension becomes poor, and deposition and accumulation occur easily during still standing, which cannot meet the requirements on stability. Moreover, since the lymphatic vessel has an opening of about 150 nm, large carbon-iron nanoparticles having the particle size of garter than 300 nm may block the lymphatic vessel probably, which causes impossibility of subsequent carbon-iron nanoparticles to pass through the lymphatic vessel and thus reduces the tracing effect and treatment effect. Therefore, by taking the stability and pharmacological efficacy of the preparation into consideration, the particle size range of the nanocarbon-iron composite is controlled within 90-300 nm, preferably within 100-250 nm, and more preferably within 120-180 nm.

In addition to adjusting the pH value of the suspension, sodium citrate added in the preparation process also uses as an anticoagulant to guarantee that the suspension can have certain fluidity after injection, thereby allowing the nanocarbon-iron composite to transfer effective components into cells.

The composite contains ferrous irons and ferric irons, which are main active ingredients that exert an anti-cancer effect by "ferroptosis", and apoptosis induced by polarization of macrophages M2 to macrophages M1. The iron in the composite may come from organic or inorganic iron salts, such as ferrous sulfate, ferric sulfate, ferrous chloride, ferric chloride, iron sucrose, ferrous succinate, ferrous gluconate, iron dextran, iron sorbitol, ferrous fumarate and ammonium ferric citrate, and preferably ferrous sulfate.

In the nanocarbon-iron composite system, the nanocarbon has a larger specific area, a large number of voids and a relatively high adsorption capacity, and the Van der Waals force, complexation and electrostatic interaction exit between an oxygen-containing group on the surface of the nanocarbon and ferric ions. In addition, carbon-iron adsorption and binding strength is moderate, and ferrous ions undergo Fenton Reaction after the nanocarbon-iron composite is phagocytosed by macrophages of tumors. Therefore, the nanocarbon-iron composite is preferably divalent iron salt, and more preferably ferrous sulfate.

The present invention also provides the range of a mass ratio of carbon nanoparticles to ferrous sulfate, which is a key factor for the nanocarbon-iron composite to exert the anti-cancer effect and is mainly obtained through pharmacological experiments. High doses of iron are directly cytotoxic to in-vitro and in-vivo tumor cells. Therefore, the dosage of iron needs to be selected reasonably. It has been proved by multiple experiments that a relatively high inhibition ratio for tumor cells is achieved when the mass ratio of nanocarbon to iron is 9.2:1 and thus the ratio of nanocarbon to iron is designed to be 3:1-40:1 in the pharmacological experiments. The results show that when the ratio of nanocarbon to iron is 5:1-30:1, the relatively high tumor inhibition ratio is achieved and is up to 50-80%, when the ratio of nanocarbon to iron is greater than 30:1, the tumor inhibition ratio is low; and when the ratio of nanocarbon to iron is less than 5:1, there is slight toxicity. Therefore, the range of the mass ratio of nanocarbon to iron in the composite is 5:1-30:1 and preferably 6:1-18:1.

Under the guidance of the above theoretical analysis, a cell experiment and an animal experiment are performed on the above samples as follows.

1. Experimental Materials
1) Cell Strains
SMMC7721 liver cancer cells, A549 lung cancer cells, SGC-7901 stomach cancer cells, HCT116 colon cancer cells, MDA-MB-231 breast cancer cells, Hela cervical cancer cells, TPC-1 thyroid cancer cells, SKOV3 ovarian cancer cells, and murine liver cancer H22 cells.

2) Cell Culture Media
DMEM cell-culture medium, RMP11640 cell-culture medium, fetal bovine serum (FBS), a typsin-EDTA solution, a mixed solution of penicillin and streptomycin and phosphate buffered saline (PBS, pH 7.4).

3) Experimental Animals
Female BalB/c-nu mice aged 4-6 weeks and with the body weight of 20±2 g are used and are allowed for free drinking and eating during the experiment. The mice are illuminated for 12 hours every day and are raised by mouse cages (5 mice/cage) which are independently ventilated and isolated.

Female inbred strain Kunming mice of clean grade aged 6-7 weeks with the body weight of 20±2 g are used, allowed for free drinking and eating during the experiment, and illuminated for 12 hours every day. Mouse cages (5 mice/cage) are ventilated by a central ventilation system.

4) Experimental Drugs and Main Instruments
A nanocarbon-iron suspension (the ratio of nanocarbon to ferric ions=9.2:1), a nanocarbon suspension, ferrous sulfate, ferrous gluconate, iron sucrose, ammonium ferric citrate, a cis-platinum injection, a 0.9% sodium chloride injection, a Prussian-blue staining kit, nuclear fast red staining liquor, xylene, anhydrous ethanol, hydrochloric acid, neutral gum, a dehydrator, an embedding machine, a pathological microtome, a tissue slicer, a high-speed centrifuge, a blast drying oven, a thermostat water bath, an inverted fluorescence microscope, a biological optical microscope, a constant-temperature incubator, a pure water filter, a high-pressure sterilizing pot, a super-clean bench, a microplate reader and an electronic scale.

2. Experimental Methods
1) Cell Experiment
Cells growing in a log phase are collected, the concentration of the cell suspension is adjusted, 100 μL of cell suspension is added to each well and the cells are plated (edge wells are filled with sterile PBS) at a density of $1 \times 10^3$-$10^4$ cells/well. The cells are incubated for 24 hours at 37° C. under the condition of 5% CO2, a nanocarbon-iron solution having a concentration gradient (nanocarbon content: 125, 62.5, 15.63 and 3.91 μg/mL; and ferric ion content: 13.65, 6.83, 1.71 and 0.43 μg/mL) is added, and three sub-wells are set. Then the cells are incubated for 48 hours at 37° C. under the condition of 5% CO2. 10 μL of CCK8 solution is added to each well and then the cells are continuously incubated for 2 hours. The absorbance of each well is measured at OD=450 nm with the microplate reader. In addition, a negative control group, nanocarbon control groups having the same concentration and iron preparation control groups having the same concentration are set.

Cells growing in a log phase are collected, the concentration of the cell suspension is adjusted, and 1 μL of cell suspension is added to each well of a 6-well plate at a density of $3 \times 10^4$ cells/well. The cells are incubated for 24 hours at 37° C. under the condition of 5% CO2, a nanocarbon-iron solution having a concentration gradient (nanocarbon content: 125, 62.5, 15.63 and 3.91 μg/mL; and ferric ion content: 13.65, 6.83, 1.71, 0.43 μg/mL) is added, and three sub-wells are set. Then the cells are incubated for 48 hours at 37° C. under the condition of 5% CO2. The cells are trypsinized and counted. In addition, a negative control group, nanocarbon control groups having the same concentration and iron preparation control groups having the same concentration are set.

2) Tumor Growth Inhibition Experiments

Cells growing in a log phase are collected, the concentration of the cell suspension is adjusted to $3\times10^7$ cells/mL, and the cell suspension is inoculated subcutaneously into the right upper extremities of nude mice at the inoculation dosage of 0.1 mL (about $3\times10^6$ cells) per mouse. When the average tumor volume of the inoculated mice reaches 100 mm$^3$, the tumor-bearing mice are randomly divided into the following groups (8 nude mice per group): a negative control group (0.9% sodium chloride injection), a nanocarbon control group, an iron preparation control group, a nanocarbon-iron suspension experimental group, and a cis-platinum control group (intraperitoneal injection at the dosage of 5 mg/kg). The above various drugs are injected into the tumors. The tumor volume changes are recorded, and the formula for calculating the volume is Volume=(length×the square of width)/2.

Milky white and thick ascites is extracted from the H22 tumor-bearing mice, the concentration of the cell suspension is adjusted to be $3\times10^7$ cells/mL, 0.1 mL of cell suspension (about $3\times10^6$ cells) is inoculated subcutaneously into the right upper extremity of each of Kunming mice. When the average tumor volume of the inoculated mice reaches 100 mm$^3$, the tumor-bearing mice are randomly divided into the following groups (8 mice per group): a negative control group (0.9% sodium chloride injection), a nanocarbon control group, an iron preparation control group, a nanocarbon-iron suspension experimental group, and a cis-platinum control group (intraperitoneal injection at the dosage of 5 mg/kg). The above various drugs are injected into the tumors. The tumor volume changes are recorded, and the formula for calculating the volume is Volume=(length×the square of width)/2.

3) Lymph Node Metastasis Inhibition Experiment

Cells growing in a log phase are collected, the concentration of the cell suspension is adjusted to $3\times10^7$ cells/mL, the cell suspension is inoculated subcutaneously into the left hind foot pads of each nude mouse at the inoculation volume of 0.05 mL (about $1.5\times10^6$ cells) and thus a lymph node metastasis mouse model is obtained. The mice are treated when the diameter of the tumor reaches 6-8 mm and there is no ulcer and necrosis. The mice are randomly divided into four groups (10 mice per group): a negative control group (0.9% sodium chloride injection), a nanocarbon control group, an iron preparation control group and a nanocarbon-iron suspension experimental group. 10 days after inoculation, the mice are killed, and popliteal lymph nodes are collected, weighed and fixed for pathological examination.

Milky white and thick ascites is extracted from the H22 tumor-bearing mice, the concentration is adjusted to be $3\times10^7$ cells/mL, 0.05 mL of cell suspension (about $1.5\times10^6$ cells) is inoculated subcutaneously into the left hind foot pads of each Kunming mouse, and thus a lymph node metastasis mouse model is obtained. The mice are treated when the diameter of the tumor reaches 6-8 mm and there is no ulcer and necrosis. The mice are randomly divided into four groups (10 mice per group): a negative control group (0.9% sodium chloride injection), a nanocarbon control group, an iron preparation control group and a nanocarbon-iron suspension experimental group. 10 days after inoculation, the mice are killed, and popliteal lymph nodes are collected, weighed and fixed for pathological examination.

4) Intracellular Distribution Experiment about Ferric Ions

Cells growing in a log phase are collected, the concentration of the cell suspension is adjusted, after cover glass is added to each well, and 1 mL of cell suspension is added to each well of a 6-well plate at a density of $3\times10^4$ cells/well. The cells are incubated for 24 hours at 37° C. under the condition of 5% CO2, a nanocarbon-iron solution having a concentration of 125:13.65 µg/mL is added, and three sub-wells are set. Then the cells are incubated for 48 hours at 37° C. under the condition of 5% CO2. 1 mL of 4% paraformaldehyde solution is added to each well, the cells are fixed for 30 minutes, and Prussian-blue staining is performed.

In the H22 subcutaneous tumor experiment, after observation for 3 weeks, tumors in the negative group, the nanocarbon group, the ferrous sulfate group and the nanocarbon-ferrous sulfate group are taken, fixed and subjected to Prussian blue staining, and then the ferric ions in the tumors are observed.

5) Mouse Lymph Node Tracing Experiment 50 ul of drug is injected into foot pads of each KM mouse, and 10 minutes later, the mice are killed, the popliteal lymph nodes, common iliac lymph nodes and paraaortic lymph nodes of mice are dissected, scored and photographed. The scoring standard is that the lymph node is completely stained with black for 1 point, is partially stained with black for 0.5 point and is not stained with black for 0 point.

3. Experimental Results

1) Results about Cell Experiments

Figure 43:
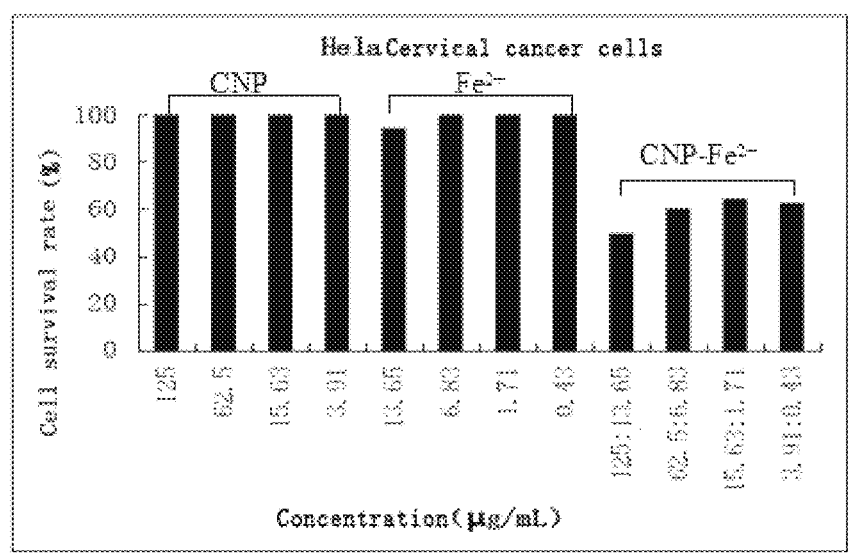
FIG. 43 is a diagram showing the cell survival rate after the nanocarbon-ferrous sulfate composite system group acts on Hela cells.

By simultaneously examining the inhibition effects of mixtures of nanocarbon with ferrous sulfate, ferrous gluconate, ammonium ferric citrate and iron sucrose respectively, it can be seen from the results that in the four iron preparations, the nanocarbon-ferrous sulfate mixture has the strongest inhibition effect and has the best effect on Hela cells, SMMC-7721 liver cancer cells and H22 liver cancer cells, and the cell survival rate is 49.54%-61.26%, namely the inhibition ratio is 39.74%-50.46%. The results are shown in tables 18-21 and FIG. 43 shows the cell survival rate 48 hours after nanocarbon-ferrous sulfate acts on the Hela cells, which is 49.54%.

TABLE 18

The cell survival rates after nanocarbon-ferrous sulfate acts on various cancer cells

| Group | Concentration (µg/mL) | Cell Survival Rate | | | | | | | | |
|---|---|---|---|---|---|---|---|---|---|---|
| | | MDA-MB-231 | Hela | SMMC-7721 | A549 | SGC-7901 | HCT116 | TPC-1 | SKOV3 | H22 |
| Nanocarbon | 125 | 100 | 100 | 100 | 100 | 100 | 100 | 100 | 100 | 100 |
| | 62.5 | 100 | 100 | 98.56 | 100 | 100 | 96.18 | 96.75 | 93.68 | 96.45 |
| | 15.63 | 100 | 100 | 99.87 | 98.16 | 100 | 99.86 | 98.54 | 94.67 | 93.47 |
| | 3.91 | 100 | 100 | 100 | 100 | 95.46 | 100 | 100 | 97.84 | 97.14 |
| Ferrous Sulfate | 13.65 | 100 | 93.99 | 97.46 | 100 | 100 | 94.07 | 93.64 | 96.47 | 100 |
| | 6.83 | 100 | 100 | 100 | 95.12 | 98.42 | 97.68 | 98.75 | 95.78 | 97.16 |
| | 1.71 | 100 | 100 | 100 | 94.18 | 93.78 | 100 | 100 | 100 | 95.24 |
| | 0.43 | 100 | 100 | 100 | 100 | 100 | 98.32 | 100 | 97.89 | 100 |
| Nanocarbon-Ferrous Sulfate | 125:13.65 | 78.1 | 49.54 | 61.26 | 84.65 | 80.14 | 75.46 | 70.69 | 76.98 | 56.97 |
| | 62.5:6.83 | 99.83 | 60.18 | 74.52 | 89.35 | 87.31 | 83.61 | 79.86 | 82.69 | 70.12 |
| | 15.63:1.71 | 100 | 64.56 | 88.69 | 91.78 | 92.87 | 89.78 | 84.13 | 89.41 | 86.35 |
| | 3.91:0.43 | 100 | 62.48 | 95.78 | 93.67 | 95.86 | 96.34 | 90.46 | 94.36 | 87.14 |

Table 19: The Cell Survival Rates after Nanocarbon-ferrous Gluconate acts on Various Cancer Cells

TABLE 19

The cell survival rates after nanocarbon-ferrous gluconate acts on various cancer cells

| Group | Concentration (μg/mL) | MDA-MB-231 | Hela | SMMC-7721 | A549 | SGC-7901 | HCT116 | TPC-1 | SKOV3 | H22 |
|---|---|---|---|---|---|---|---|---|---|---|
| Nanocarbon | 125 | 100 | 100 | 100 | 100 | 100 | 100 | 100 | 100 | 100 |
| | 62.5 | 98.46 | 100 | 100 | 100 | 100 | 100 | 100 | 100 | 100 |
| | 15.63 | 95.76 | 100 | 100 | 100 | 100 | 100 | 96.89 | 100 | 100 |
| | 3.91 | 100 | 100 | 100 | 97.65 | 97.61 | 100 | 100 | 98.47 | 100 |
| Ferrous Gluconate | 13.65 | 100 | 97.86 | 100 | 97.31 | 97.43 | 98.67 | 98.34 | 97.11 | 96.14 |
| | 6.83 | 100 | 100 | 97.68 | 100 | 99.48 | 100 | 100 | 96.47 | 100 |
| | 1.71 | 100 | 100 | 96.12 | 100 | 100 | 100 | 100 | 100 | 100 |
| | 0.43 | 100 | 100 | 100 | 100 | 100 | 100 | 100 | 100 | 100 |
| Nanocarbon-Ferrous Gluconate | 125:13.65 | 91.65 | 89.95 | 92.68 | 91.65 | 89.42 | 90.45 | 87.14 | 91.2 | 84.69 |
| | 62.5:6.83 | 94.68 | 95.1 | 95.32 | 97.68 | 91.23 | 93.71 | 91.32 | 95.12 | 90.68 |
| | 15.63:1.71 | 99.47 | 97.67 | 97.58 | 98.12 | 95.74 | 97.61 | 94.79 | 100 | 93.45 |
| | 3.91:0.43 | 100 | 100 | 100 | 100 | 99.78 | 100 | 98.74 | 100 | 97.36 |

Table 20: The Cell Survival Rates after Nanocarbon-iron Sucrose acts on Various Cancer Cells

TABLE 20

The cell survival rates after nanocarbon-iron sucrose acts on various cancer cells

| Group | Concentration (μg/mL) | MDA-MB-231 | Hela | SMMC-7721 | A549 | SGC-7901 | HTC116 | TPC-1 | SKOV3 | H22 |
|---|---|---|---|---|---|---|---|---|---|---|
| Nanocarbon | 125 | 100 | 100 | 100 | 100 | 100 | 100 | 100 | 100 | 100 |
| | 62.5 | 98.46 | 100 | 100 | 100 | 100 | 100 | 100 | 100 | 100 |
| | 15.63 | 95.76 | 100 | 100 | 100 | 100 | 100 | 96.89 | 100 | 100 |
| | 3.91 | 100 | 100 | 100 | 97.65 | 97.61 | 100 | 100 | 98.47 | 100 |
| Iron Sucrose | 13.65 | 100 | 97.86 | 100 | 97.31 | 97.43 | 98.67 | 98.34 | 97.11 | 96.14 |
| | 6.83 | 100 | 100 | 97.68 | 100 | 99.48 | 100 | 100 | 96.47 | 100 |
| | 1.71 | 100 | 100 | 96.12 | 100 | 100 | 100 | 100 | 100 | 100 |
| | 0.43 | 100 | 100 | 100 | 100 | 100 | 100 | 100 | 100 | 100 |
| Nanocarbon-Iron Sucrose | 125:13.65 | 91.65 | 89.95 | 92.68 | 91.65 | 89.42 | 90.45 | 87.14 | 91.2 | 84.69 |
| | 62.5:6.83 | 94.68 | 95.1 | 95.32 | 97.68 | 91.23 | 93.71 | 91.32 | 95.12 | 90.68 |
| | 15.63:1.71 | 99.47 | 97.67 | 97.58 | 98.12 | 95.74 | 97.61 | 94.79 | 100 | 93.45 |
| | 3.91:0.43 | 100 | 100 | 100 | 100 | 99.78 | 100 | 98.74 | 100 | 97.36 |

Table 21: The Cell Survival Rate after Nanocarbon-ammonium Ferric Citrate acts on Various Cancer Cells

TABLE 21

The cell survival rate after nanocarbon-ammonium ferric citrate acts on various cancer cells

| Group | Concentration (μg/mL) | MDA-MB-231 | Hela | SMMC-7721 | A549 | SGC-7901 | HCT116 | TPC-1 | SKOV3 | H22 |
|---|---|---|---|---|---|---|---|---|---|---|
| Nanocarbon | 125 | 100 | 100 | 94.79 | 99.64 | 100 | 97.64 | 100 | 100 | 100 |
| | 62.5 | 100 | 95.36 | 96.78 | 96.47 | 100 | 95.33 | 100 | 100 | 100 |
| | 15.63 | 100 | 100 | 100 | 97.13 | 100 | 100 | 100 | 100 | 100 |
| | 3.91 | 100 | 94.68 | 100 | 100 | 100 | 96.82 | 100 | 100 | 94.62 |
| Ammonium Ferric Citrate | 13.65 | 95.12 | 93.67 | 100 | 94.67 | 100 | 95.31 | 100 | 100 | 100 |
| | 6.83 | 97.28 | 97.46 | 94.19 | 95.76 | 96.41 | 94.03 | 100 | 94.36 | 95.12 |
| | 1.71 | 100 | 99.34 | 98.43 | 99.64 | 95.31 | 98.12 | 96.41 | 99.46 | 97.64 |
| | 0.43 | 100 | 100 | 100 | 97.21 | 97.85 | 97.31 | 97.30 | 95.67 | 96.21 |
| Nanocarbon-Ammonium Ferric Citrate | 125:13.65 | 88.67 | 86.14 | 83.96 | 88.74 | 86.14 | 90.36 | 87.30 | 90.25 | 84.76 |
| | 62.5:6.83 | 93.46 | 89.75 | 87.91 | 90.13 | 89.31 | 97.16 | 91.38 | 94.67 | 89.67 |
| | 15.63:1.71 | 94.69 | 94.68 | 90.15 | 96.45 | 92.46 | 94.26 | 94.87 | 100 | 91.67 |
| | 3.91:0.43 | 97.68 | 100 | 94.78 | 96.78 | 96.74 | 99.43 | 96.71 | 98.46 | 96.78 |

Tumor Growth Inhibition Results

Figure 4:
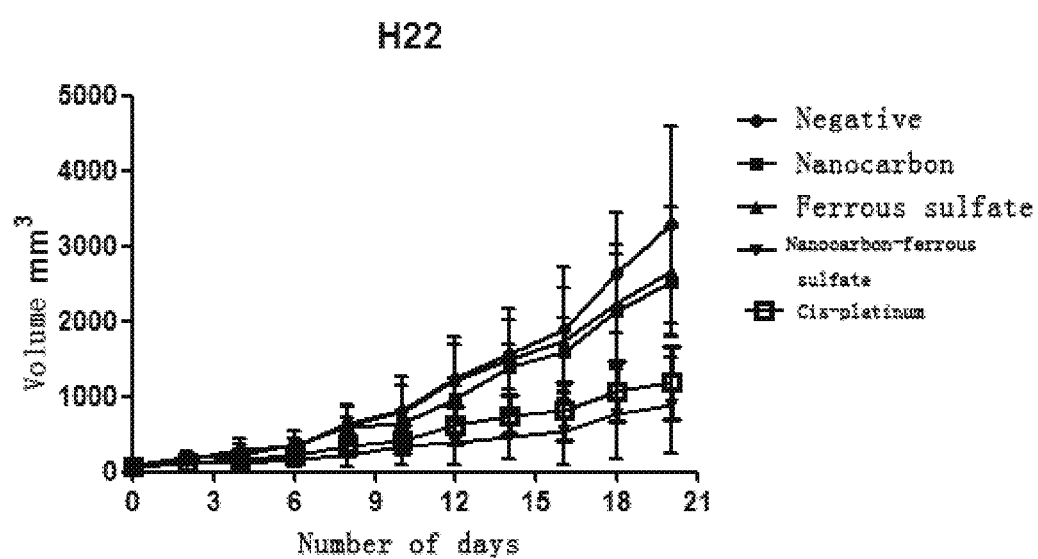
FIG. 4 is a diagram showing the growth and volume of the H22 tumors in the nanocarbon-ferrous sulfate composite system group.
Figure 5:
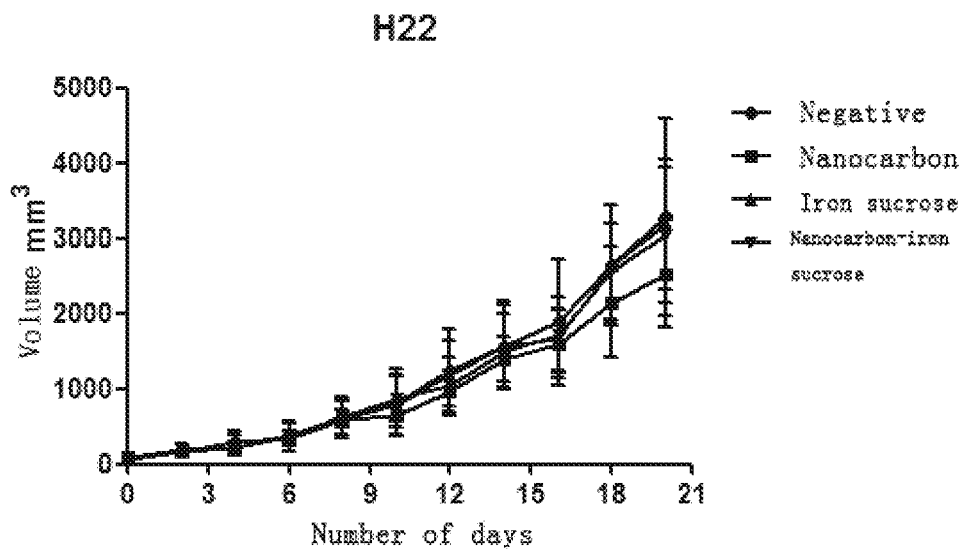
FIG. 5 is a diagram showing the growth and volume of the H22 tumors in the nanocarbon-iron sucrose composite system group.
Figure 6:
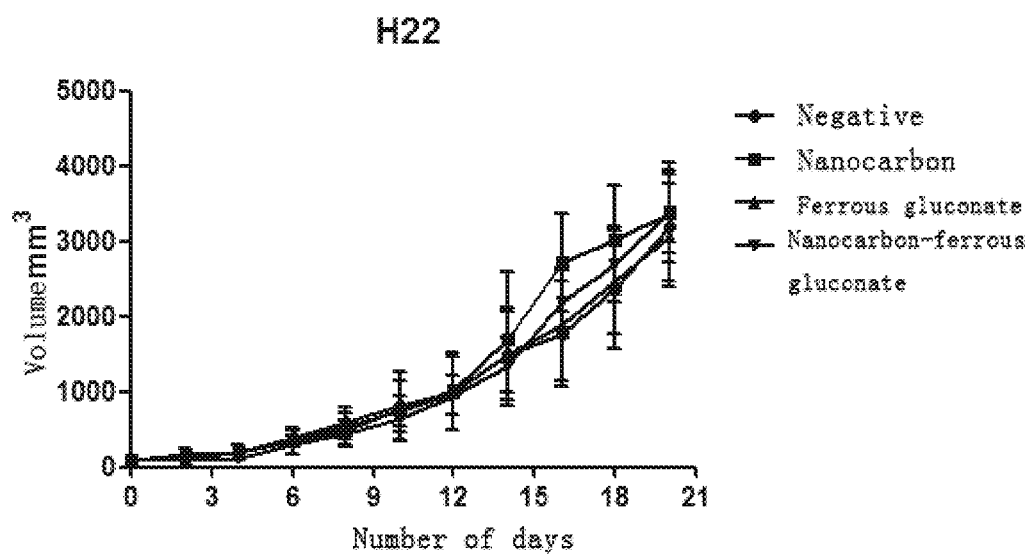
FIG. 6 is a diagram showing the growth and volume of the H22 tumors in the nanocarbon-ferrous gluconate composite system group.
Figure 7:
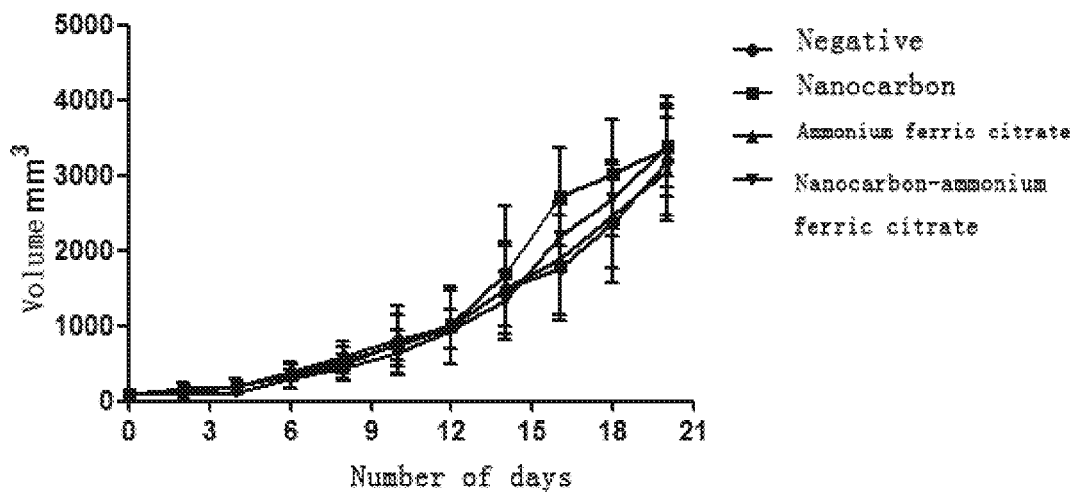
FIG. 7 is a diagram showing the growth and volume of the H22 tumors in the nanocarbon-ammonium ferric citrate composite system group.
Figure 8:
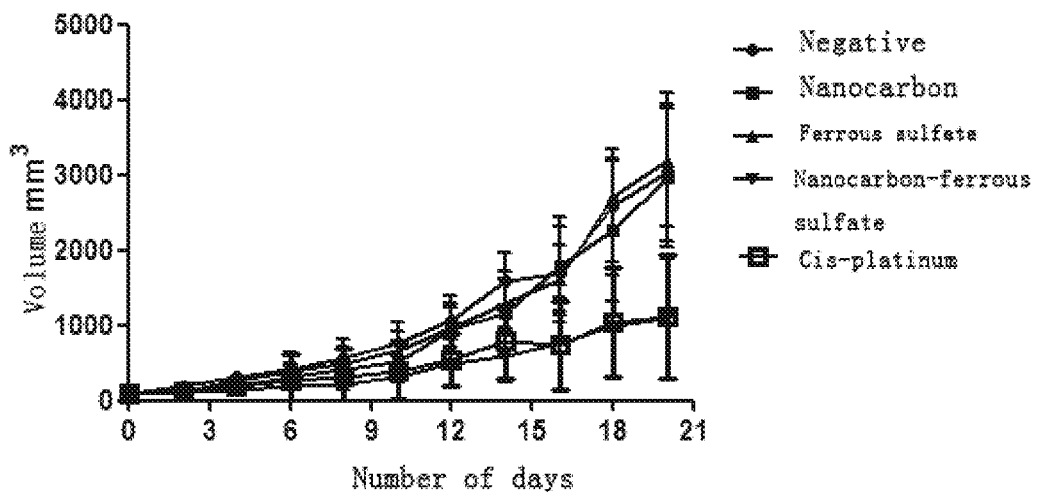
FIG. 8 is a diagram showing the growth and volume of A549 tumors in the nanocarbon-ferrous sulfate composite system group.
Figure 9:
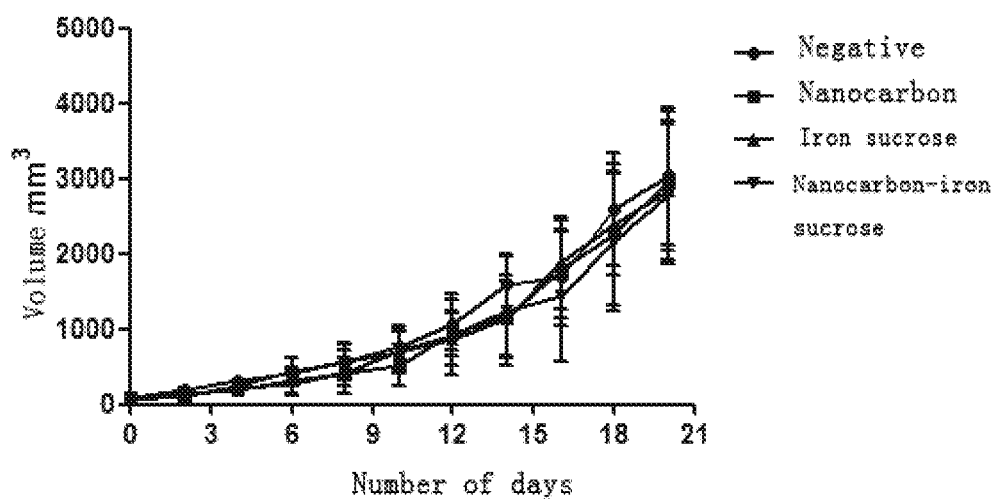
FIG. 9 is a diagram showing the growth and volume of the A549 tumors in the nanocarbon-iron sucrose composite system group.
Figure 10:
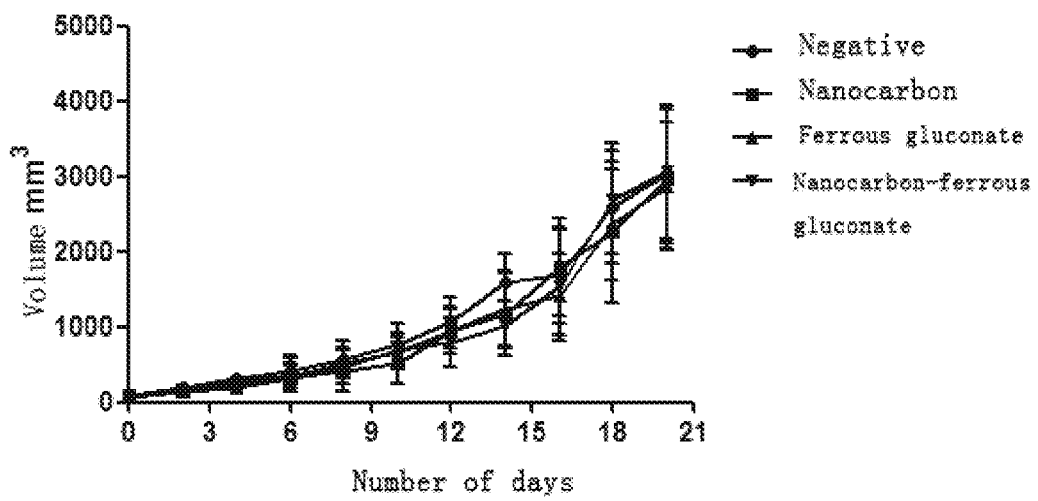
FIG. 10 is a diagram showing the growth and volume of the A549 tumors in the nanocarbon-ferrous gluconate composite system group.
Figure 11:
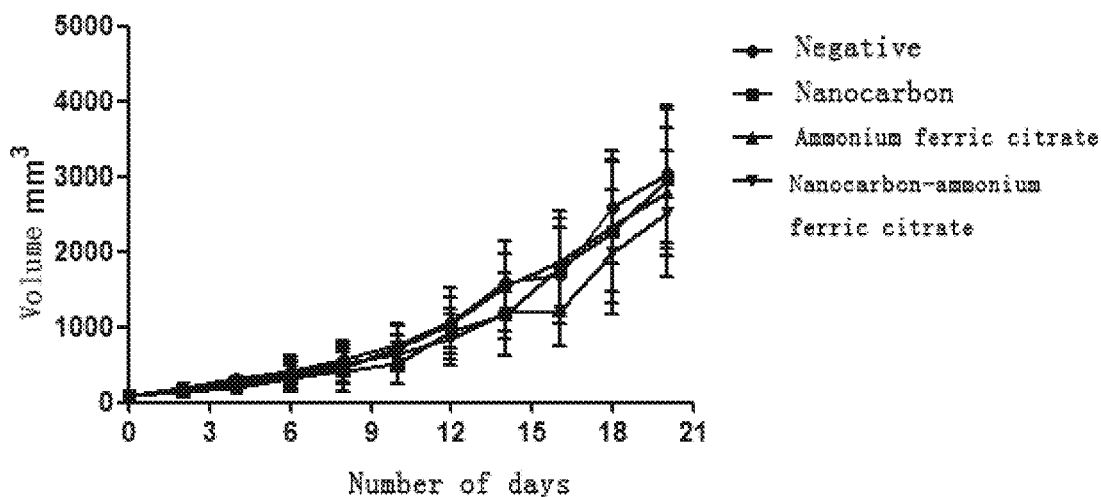
FIG. 11 is a diagram showing the growth and volume of the A549 tumors in the nanocarbon-ammonium ferric citrate composite system group.
Figure 12:
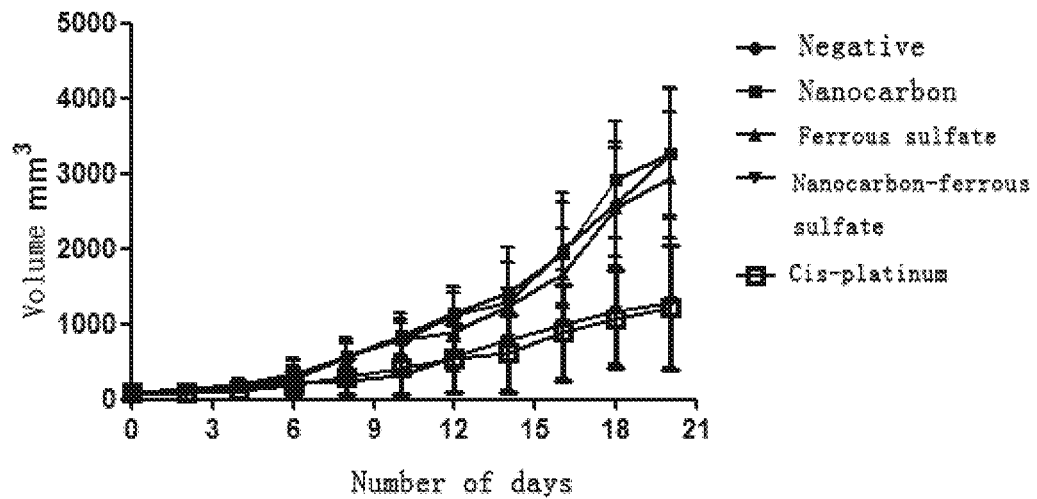
FIG. 12 is a diagram showing the growth and volume of HCT116 tumors in the nanocarbon-ferrous sulfate composite system group.
Figure 13:
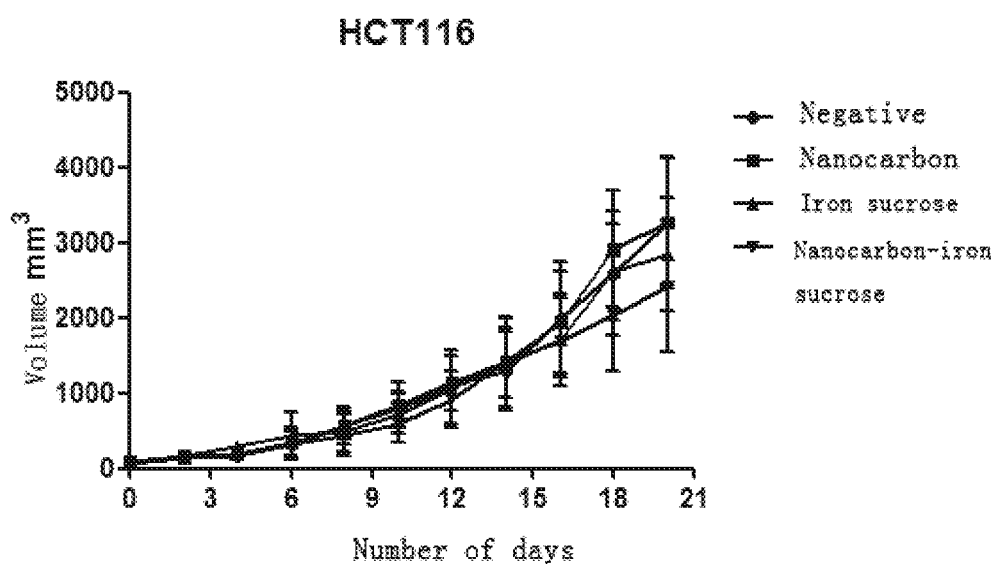
FIG. 13 is a diagram showing the growth and volume of the HCT116 tumors in the nanocarbon-iron sucrose composite system group.
Figure 14:
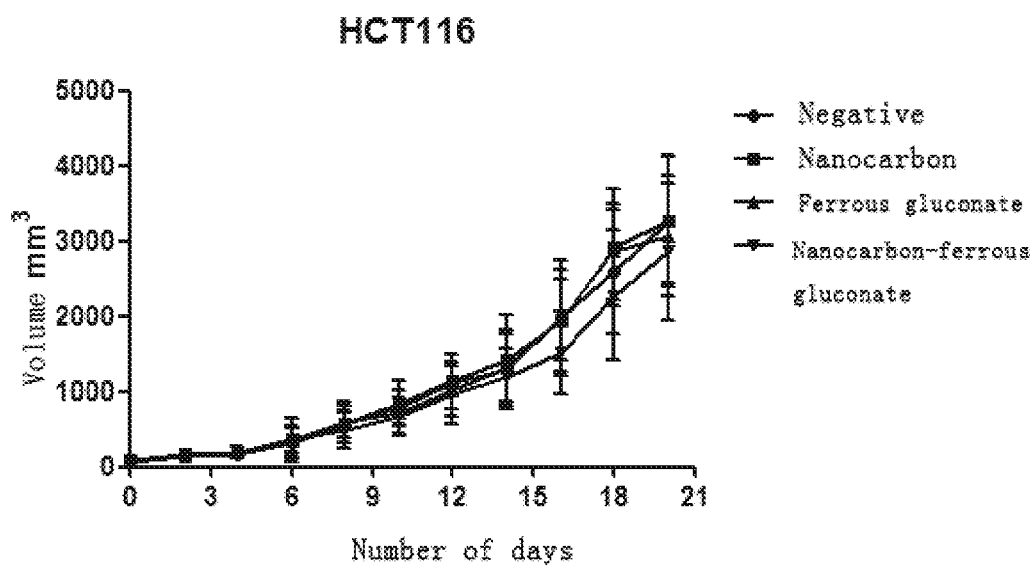
FIG. 14 is a diagram showing the growth and volume of the HCT116 tumors in the nanocarbon-ferrous gluconate composite system group.
Figure 15:
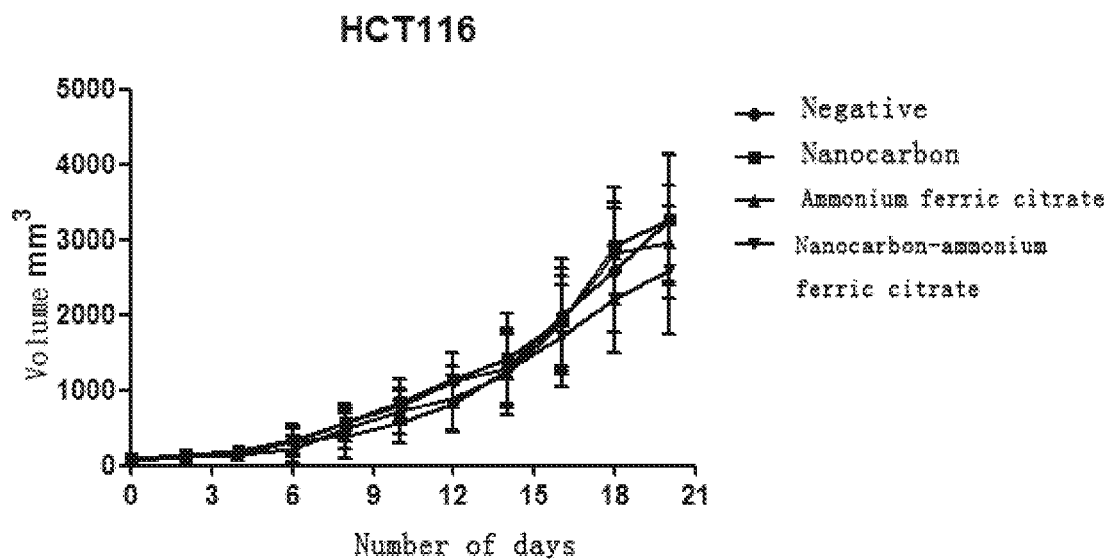
FIG. 15 is a diagram showing the growth and volume of the HCT116 tumors in the nanocarbon-ammonium ferric citrate composite system group.
Figure 16:
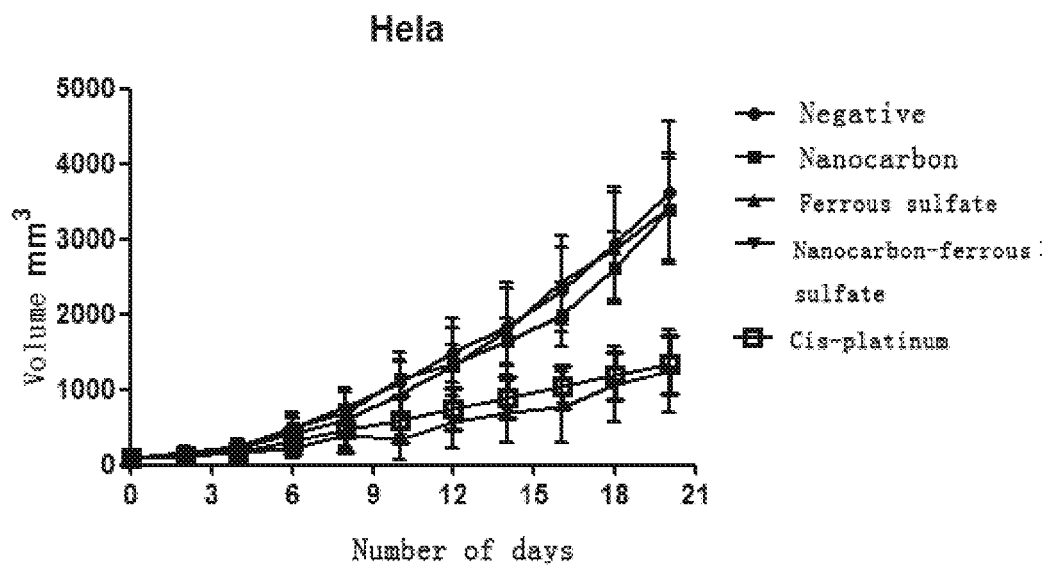
FIG. 16 is a diagram showing the growth and volume of Hela tumors in the nanocarbon-ferrous sulfate composite system group.
Figure 17:
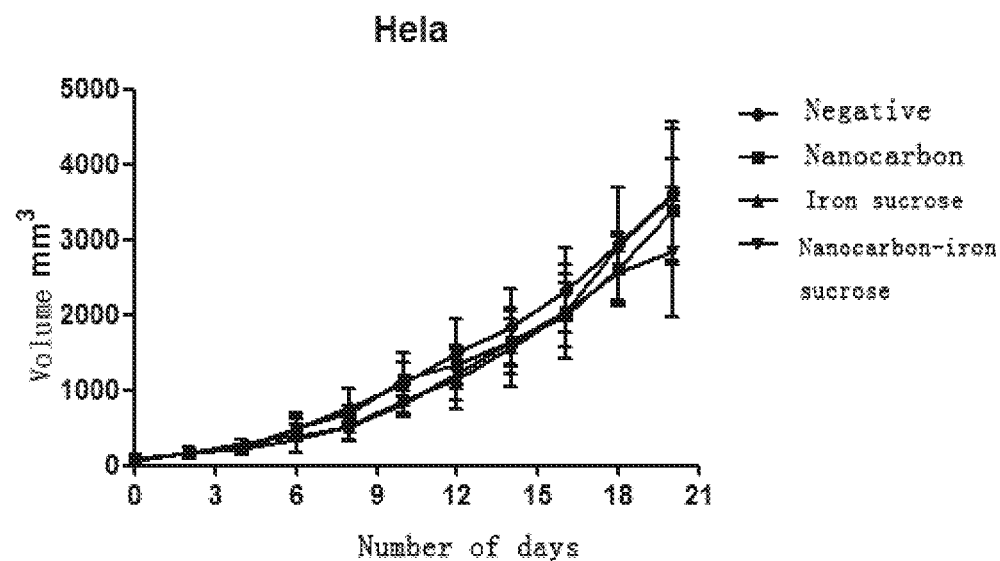
FIG. 17 is a diagram showing the growth and volume of the Hela tumors in the nanocarbon-iron sucrose composite system group.
Figure 18:
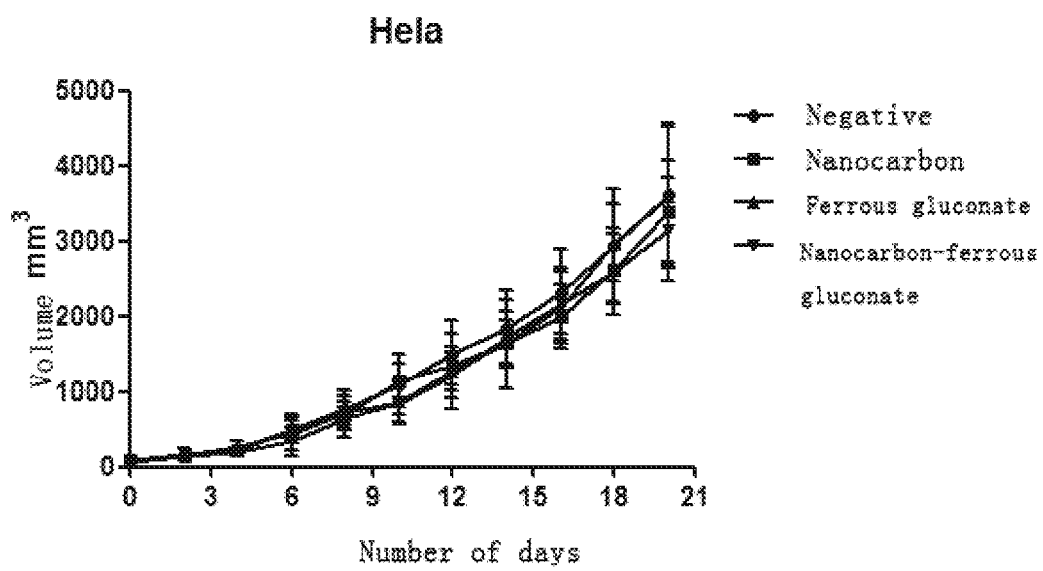
FIG. 18 is a diagram showing the growth and volume of the Hela tumors in the nanocarbon-ferrous gluconate composite system group.
Figure 19:
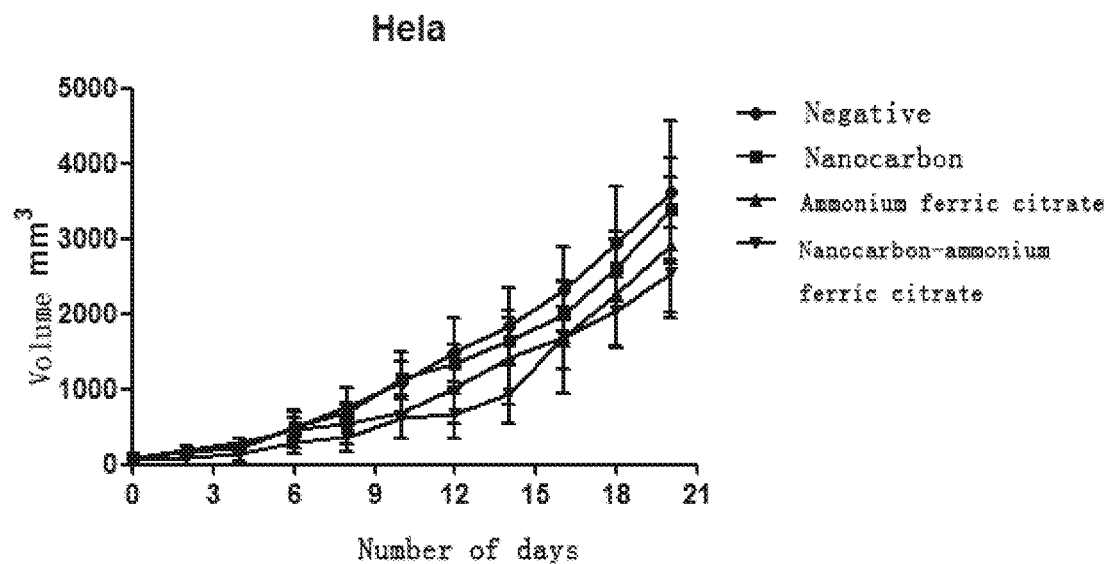
FIG. 19 is a diagram showing the growth and volume of the Hela tumors in the nanocarbon-ammonium ferric citrate composite system group.
Figure 20:
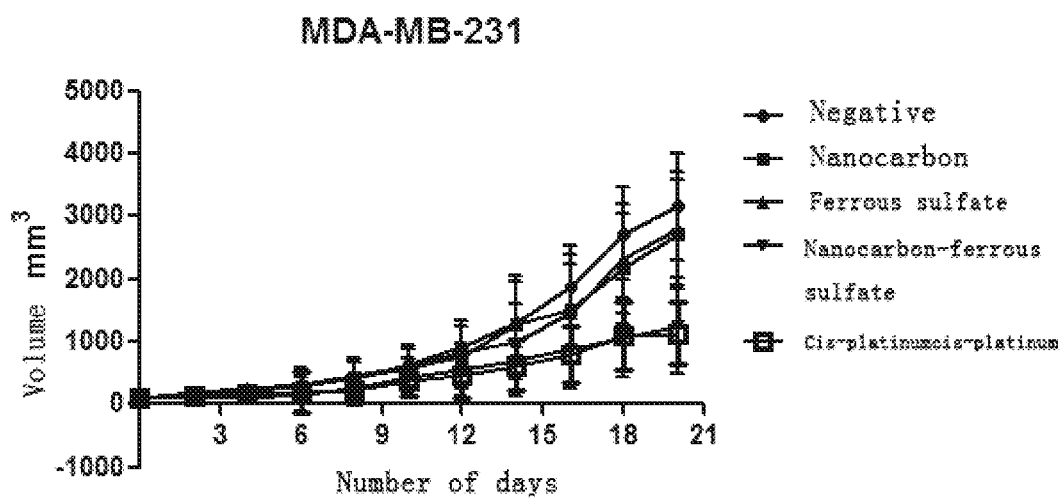
FIG. 20 is a diagram showing the growth and volume of MDA-MB-231 tumors in the nanocarbon-ferrous sulfate composite system group.
Figure 21:
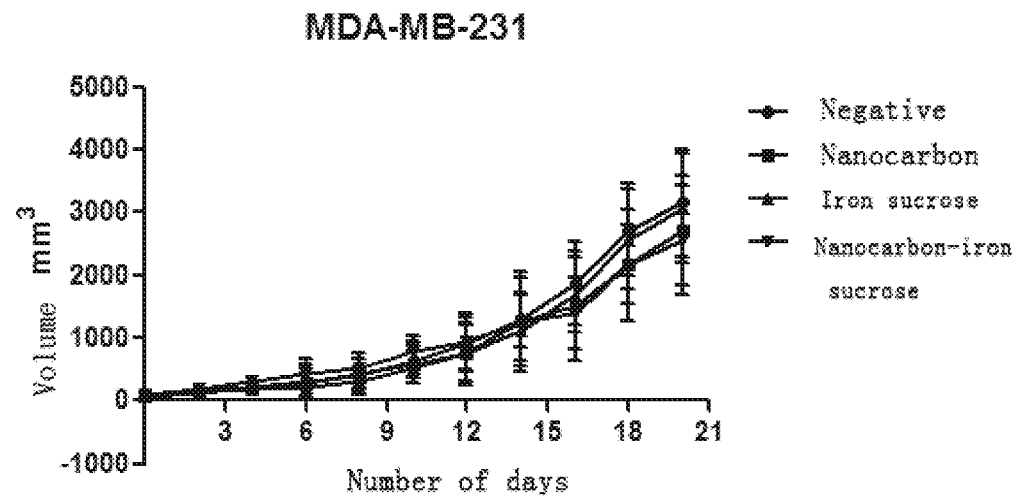
FIG. 21 is a diagram showing the growth and volume of the MDA-MB-231 tumors in the nanocarbon-iron sucrose composite system group.
Figure 22:
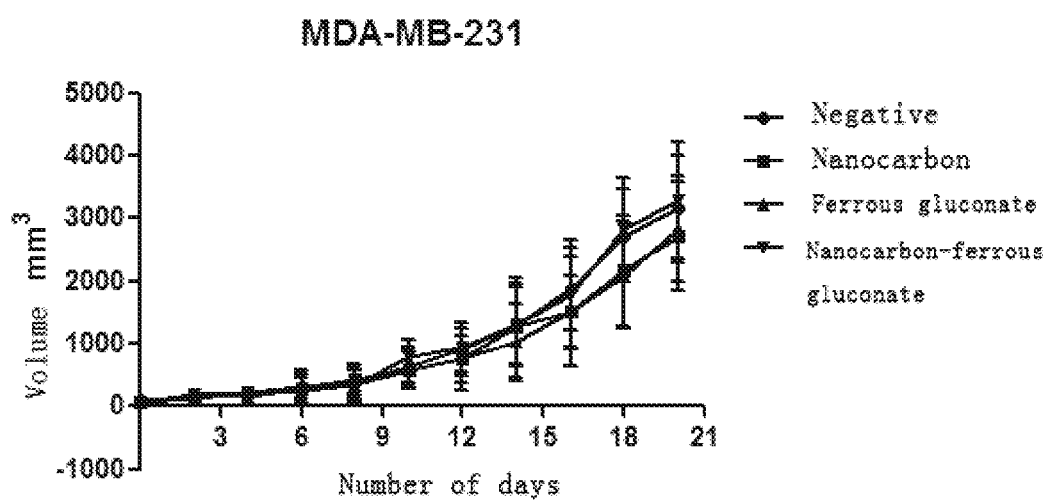
FIG. 22 is a diagram showing the growth and volume of the MDA-MB-231 tumors in the nanocarbon-ferrous gluconate composite system group.
Figure 23:
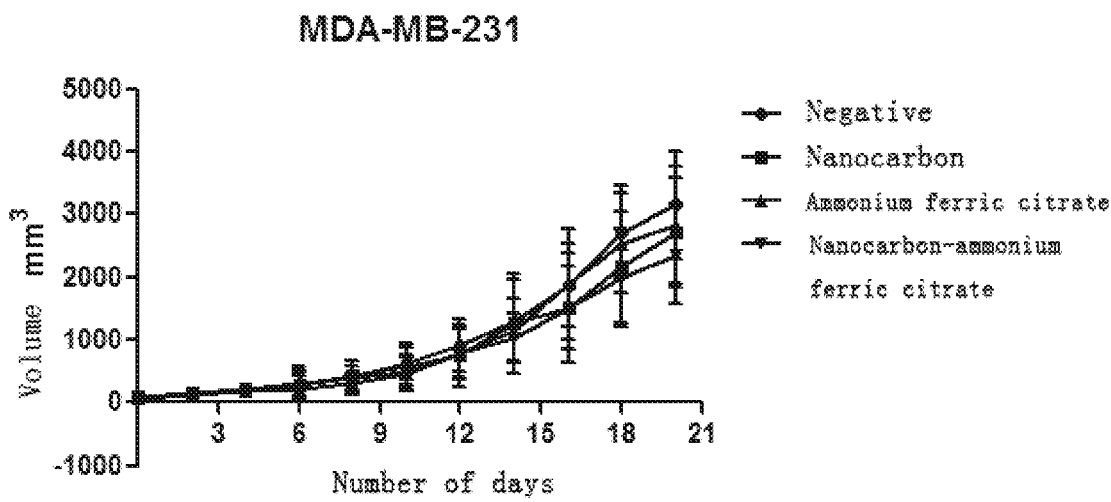
FIG. 23 is a diagram showing the growth and volume of the MDA-MB-231 tumors in the nanocarbon-ammonium ferric citrate composite system group.
Figure 24:
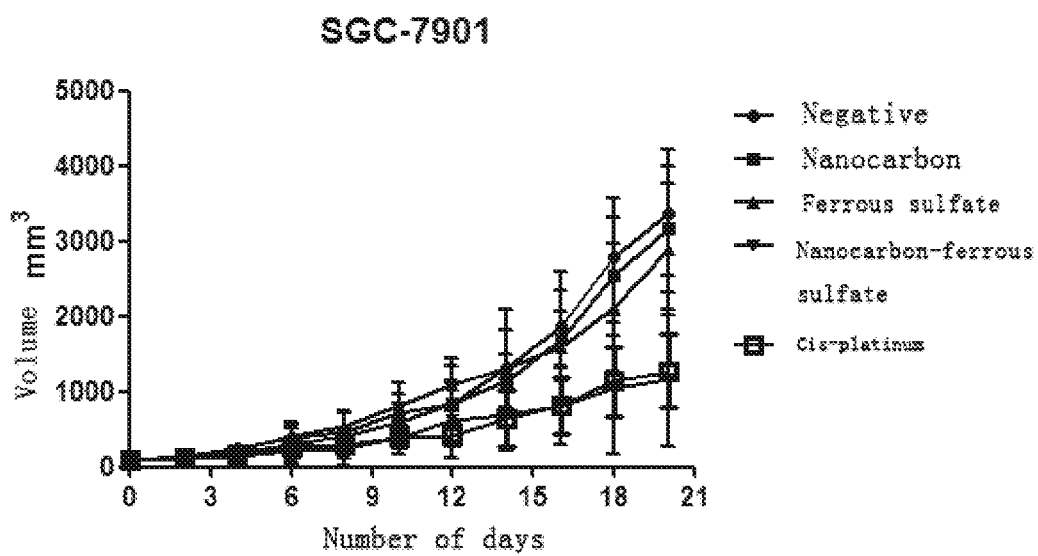
FIG. 24 is a diagram showing the growth and volume of SGC-7901 tumors in the nanocarbon-ferrous sulfate composite system group.
Figure 25:
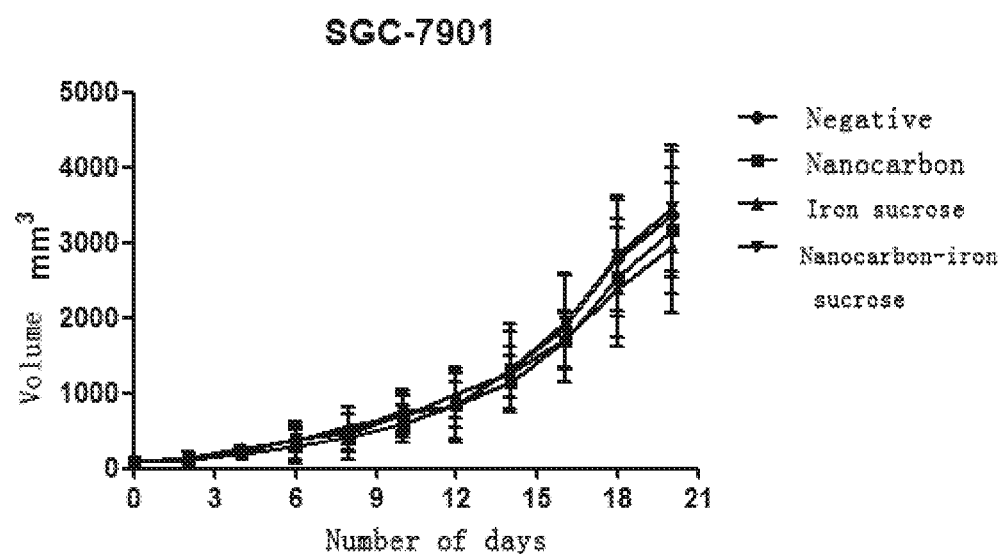
FIG. 25 is a diagram showing the growth and volume of the SGC-7901 tumors in the nanocarbon-iron sucrose composite system group.
Figure 26:
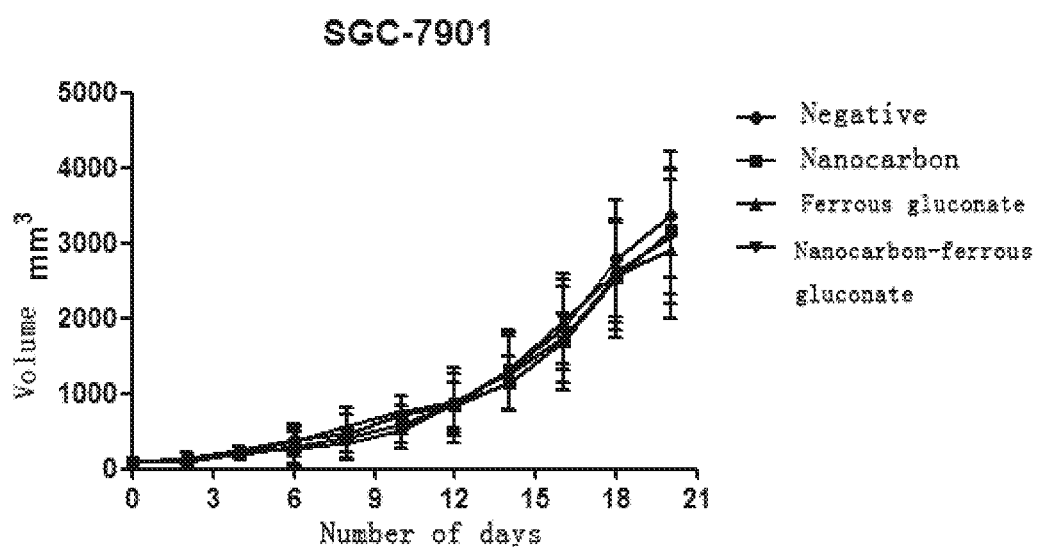
FIG. 26 is a diagram showing the growth and volume of the SGC-7901 tumors in the nanocarbon-ferrous gluconate composite system group.
Figure 27:
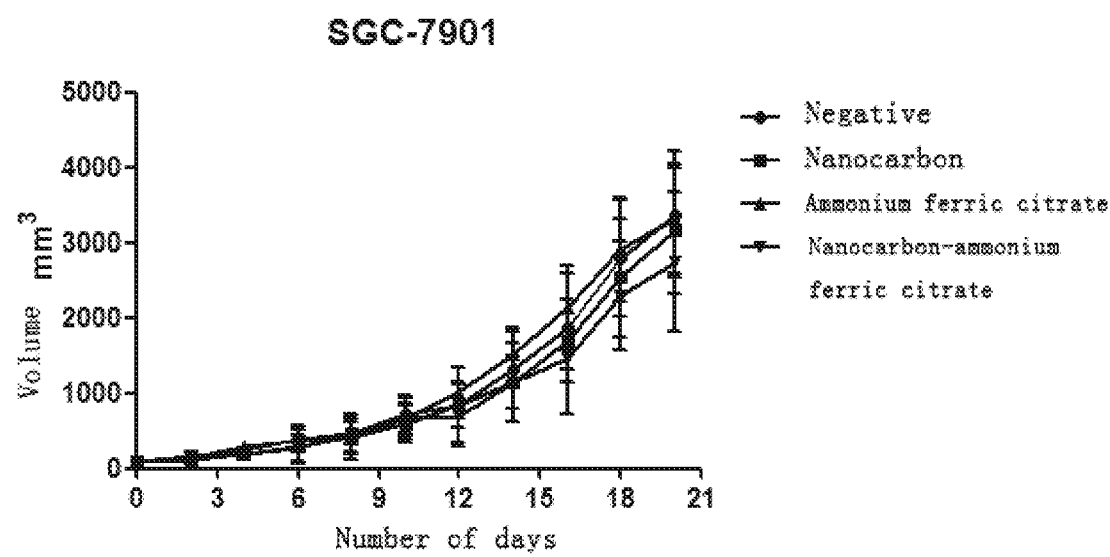
FIG. 27 is a diagram showing the growth and volume of SGC-7901 tumors in the nanocarbon-ammonium ferric citrate composite system group.
Figure 28:
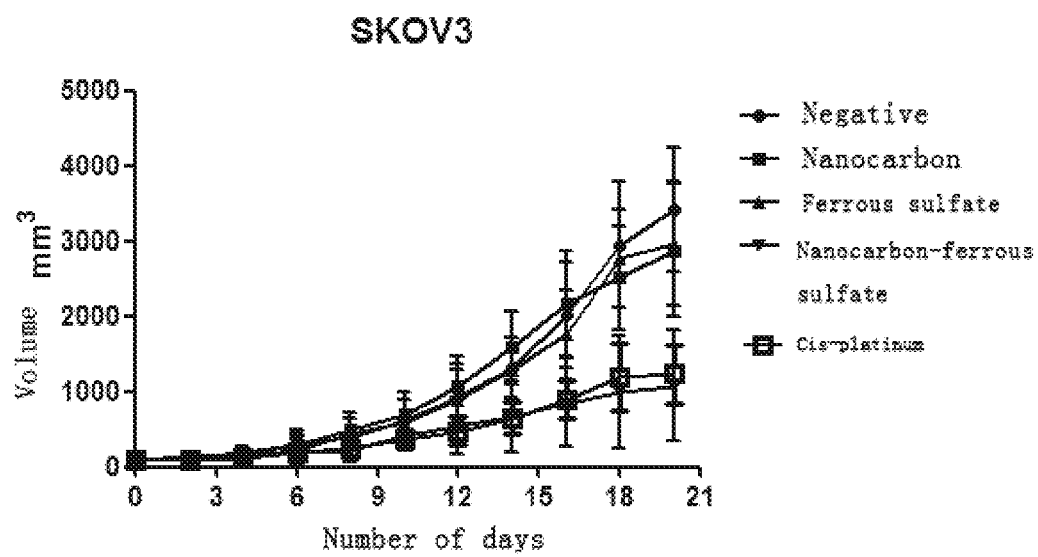
FIG. 28 is a diagram showing the growth and volume of SKOV3 tumors in the nanocarbon-ferrous sulfate composite system group.
Figure 29:
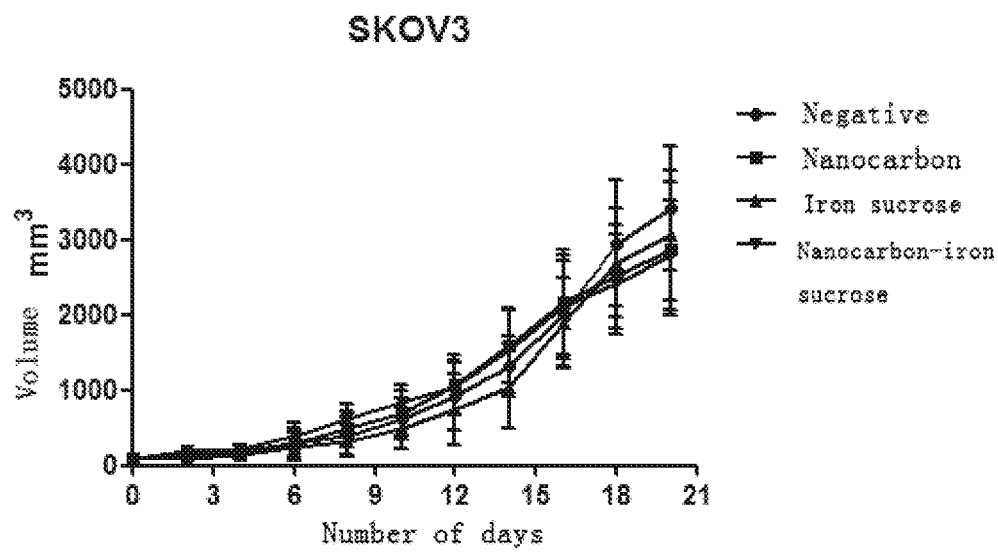
FIG. 29 is a diagram showing the growth and volume of the SKOV3 tumors in the nanocarbon-iron sucrose composite system group.
Figure 30:
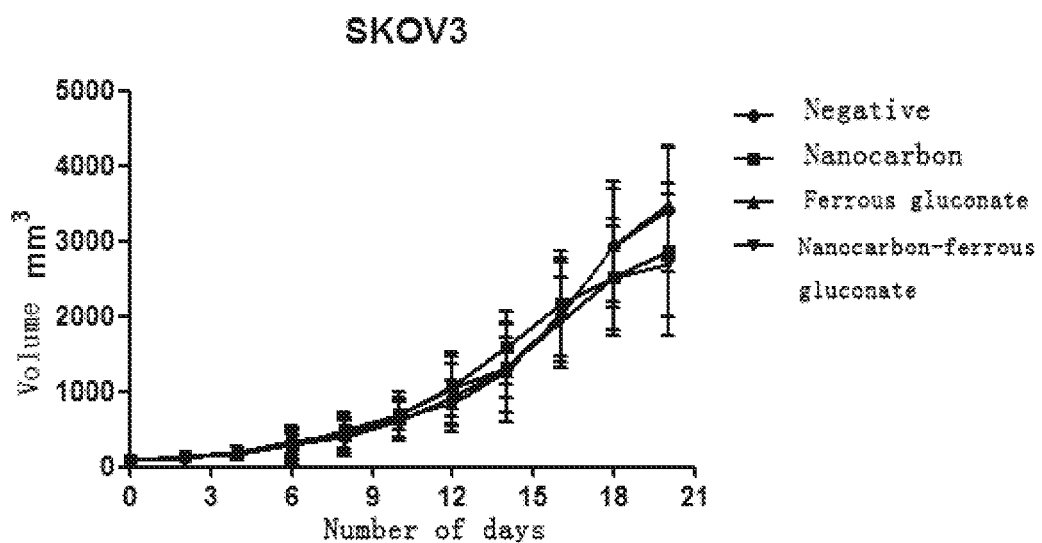
FIG. 30 is a diagram showing the growth and volume of the SKOV3 tumors in the nanocarbon-ferrous gluconate composite system group.
Figure 31:
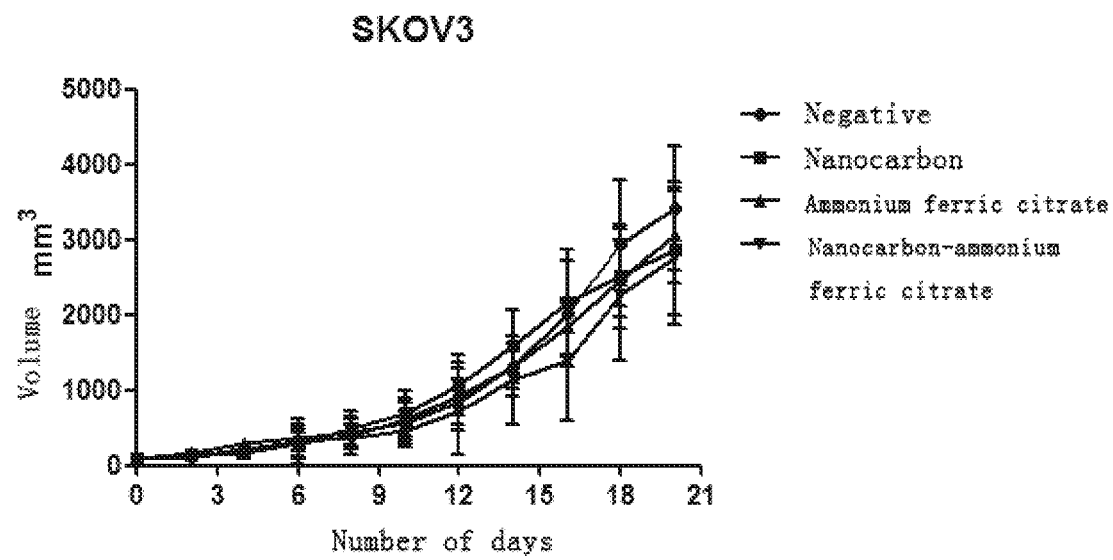
FIG. 31 is a diagram showing the growth and volume of the SKOV3 tumors in the nanocarbon-ammonium ferric citrate composite system group.
Figure 32:
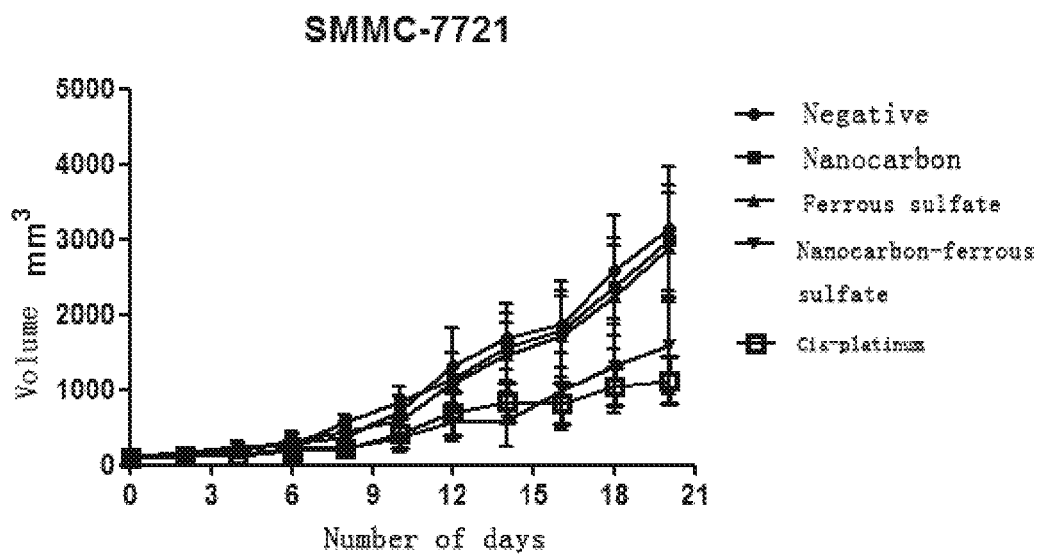
FIG. 32 is a diagram showing the growth and volume of SMMC-7721 tumors in the nanocarbon-ferrous sulfate composite system group.
Figure 33:
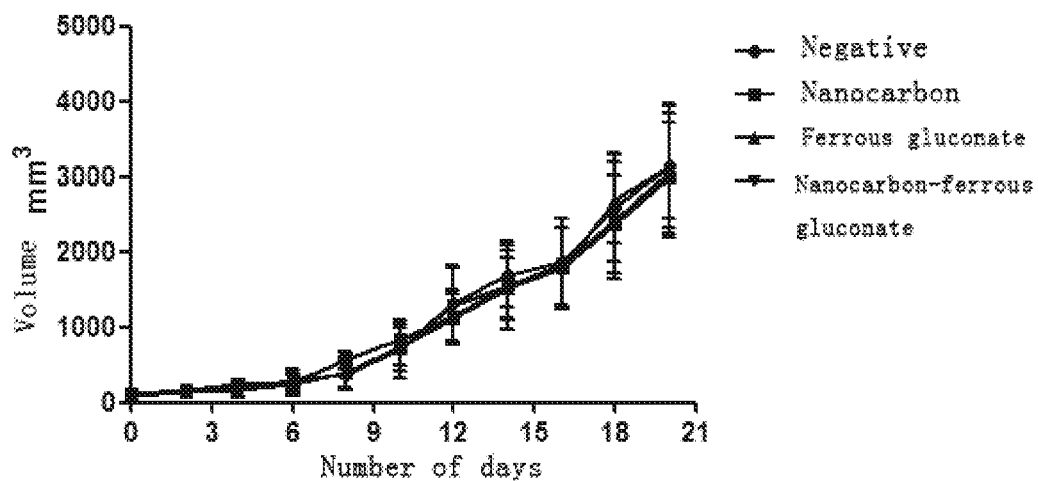
FIG. 33 is a diagram showing the growth and volume of the SMMC-7721 tumors in the nanocarbon-iron sucrose composite system group.
Figure 34:
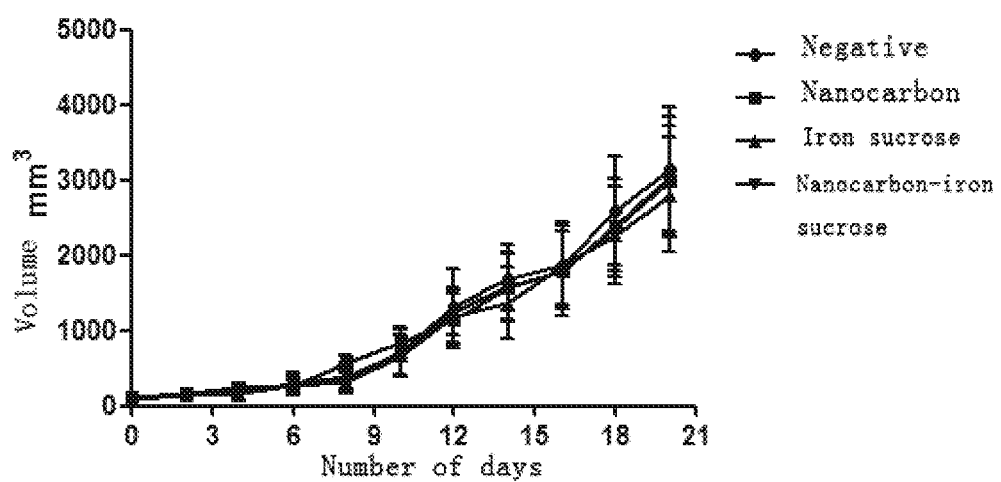
FIG. 34 is a diagram showing the growth and volume of the SMMC-7721 tumors in the nanocarbon-ferrous gluconate composite system group.
Figure 35:
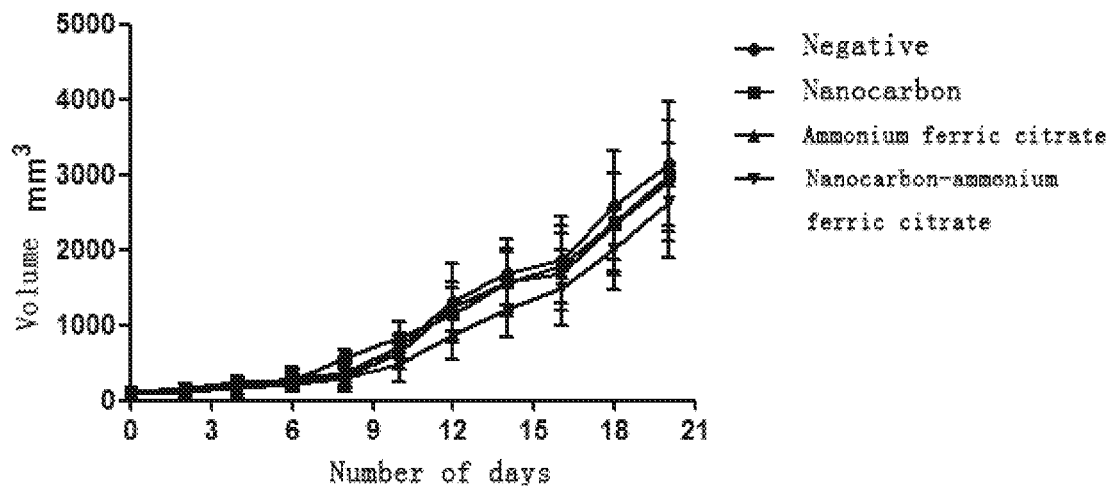
FIG. 35 is a diagram showing the growth and volume of the SMMC-7721 tumors in the nanocarbon-ammonium ferric citrate composite system group.
Figure 36:
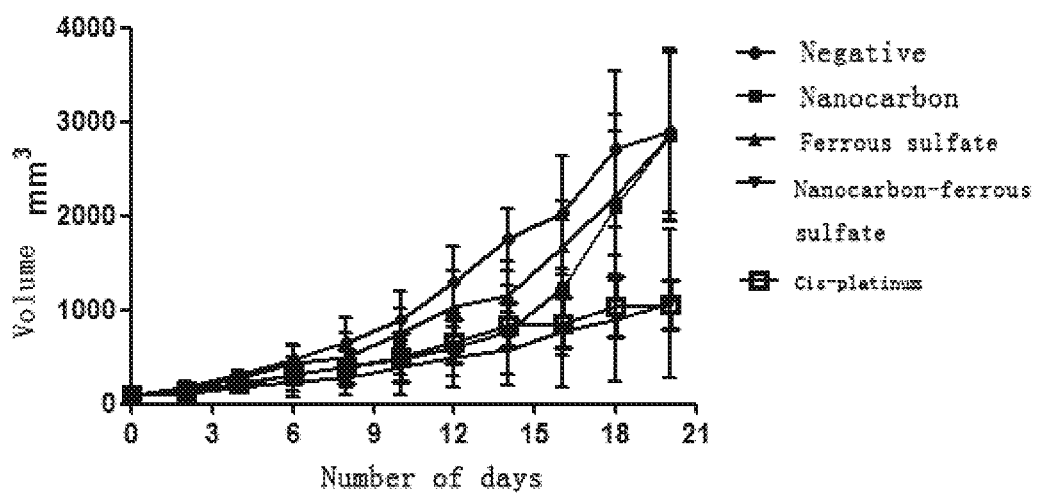
FIG. 36 is a diagram showing the growth and volume of TPC-1 tumors in the nanocarbon-ferrous sulfate composite system group.
Figure 37:
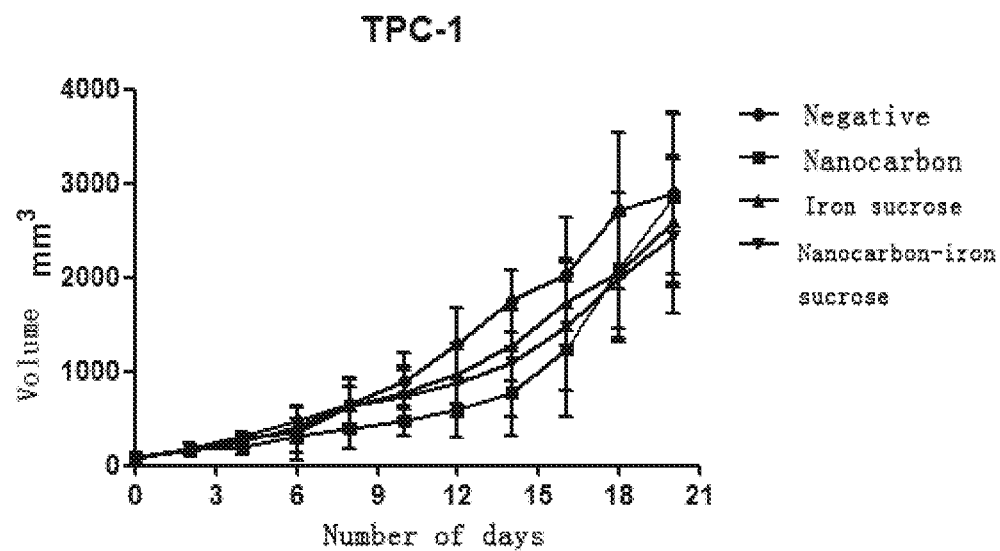
FIG. 37 is a diagram showing the growth and volume of the TPC-1 tumors in the nanocarbon-iron sucrose composite system group.
Figure 38:
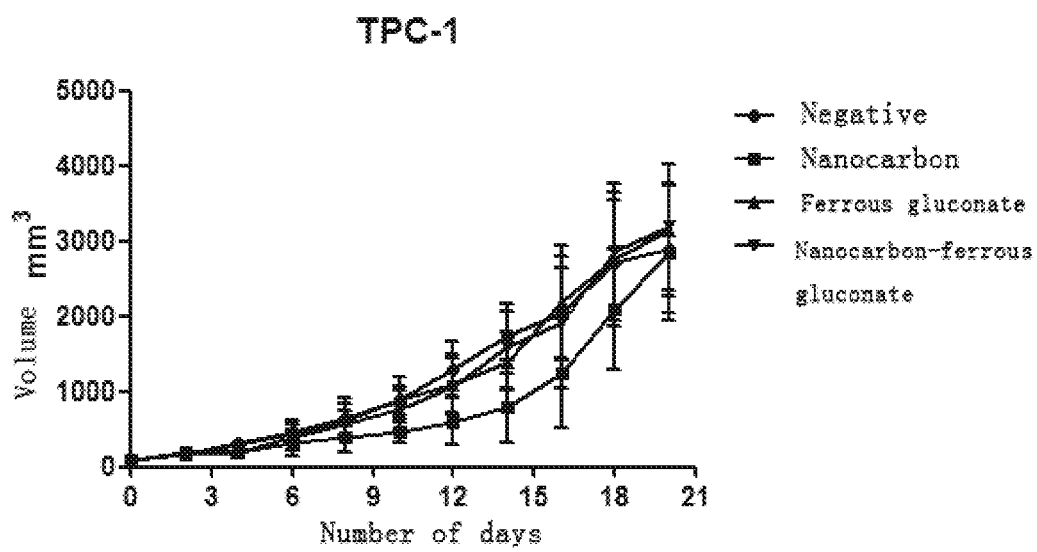
FIG. 38 is a diagram showing the growth and volume of the TPC-1 tumors in the nanocarbon-ferrous gluconate composite system group.
Figure 39:
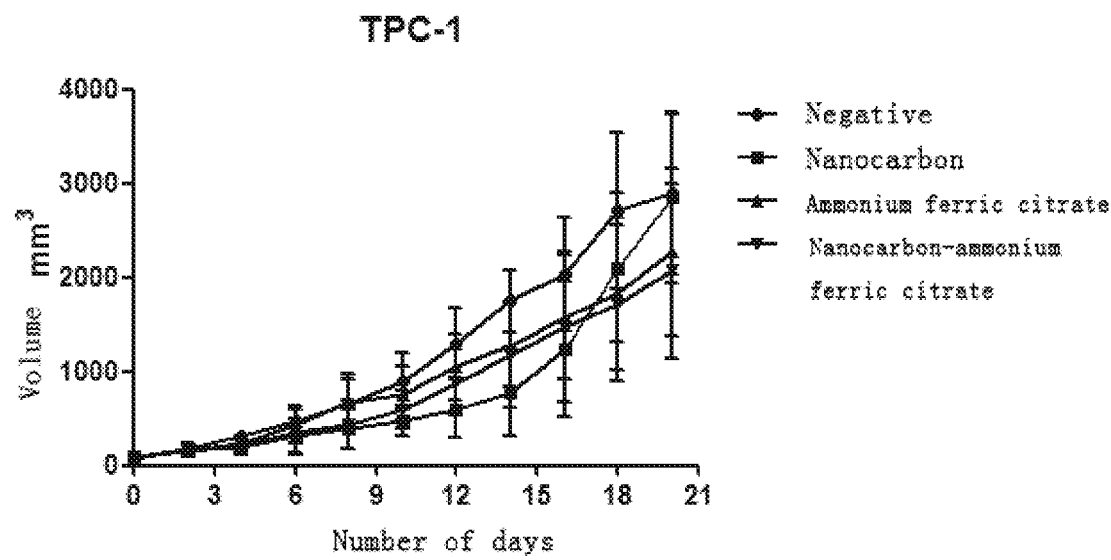
FIG. 39 is a diagram showing the growth and volume of the TPC-1 tumors in the nanocarbon-ammonium ferric citrate composite system group.

By simultaneously examining the inhibition effects of mixtures of nanocarbon with ferrous sulfate, ferrous gluconate, ammonium ferric citrate and iron sucrose respectively, the results show that in the four iron preparations, the nanocarbon-ferrous sulfate mixture has the strongest inhibition effect, and has a tumor inhibition ratio of 50-73% for various cancer cells, with the highest tumor inhibition ratio for H22 liver cancer cells that reaches 73, and the results are shown in FIG. 4. The inhibition effects of four iron preparations on subcutaneous transplantation tumors of 9 types of cancer cells are shown in FIGS. 4-39. The nanocarbon, ferrous sulfate, ferrous gluconate, ammonium ferric citrate and iron sucrose alone as well as nanocarbon-ferrous gluconate, nanocarbon-ammonium ferric citrate and nanocarbon-iron sucrose do not have an inhibition effect on growth of 9 types of tumors substantially, but the inhibition ratio of nanocarbon-ferrous sulfate for all 9 types of tumors reach at least 50%. In addition, the tumor growth inhibition effects of nanocarbon-ferrous sulfate at different mass ratios are compared. By way of example, as shown in table 22, when the nanocarbon has the concentration of 25 mg/mL, nanocarbon-ferrous sulfate has a better inhibition effect (50%-80%) at the mass ratio of 2:1-30:1, has relatively high toxicity at the mass ratio of 2:1, has light toxicity at the mass ratio of 5:1, and has a relatively poor inhibition effect on the tumor growth at the mass ratio of greater than 30:1. Thus, it is considered to select nanocarbon-ferrous sulfate at the mass ratio of 5:1-30:1, preferably 6:1-18:1.

Figure 40:
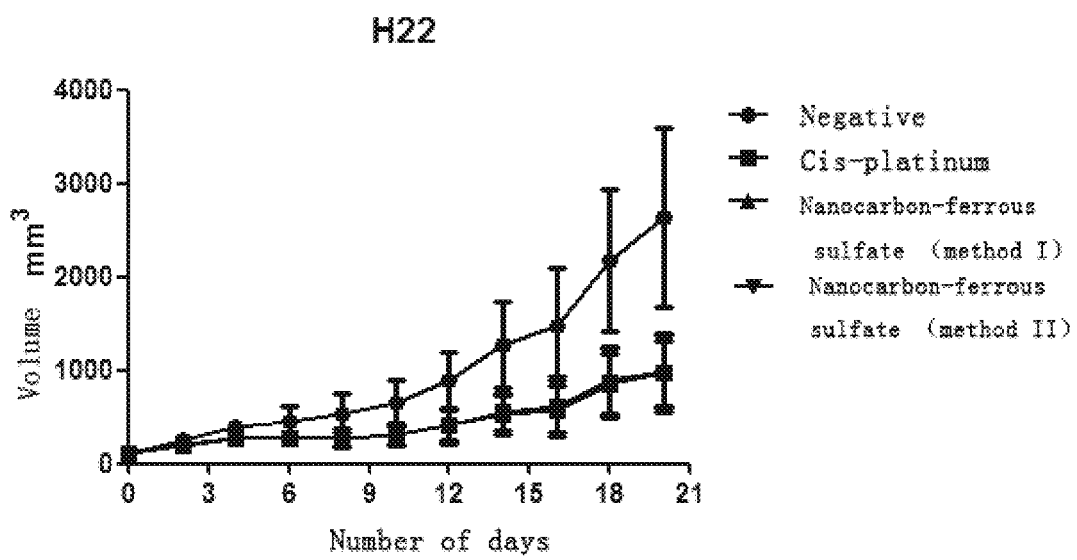
FIG. 40 is a diagram showing the growth and volume of the H22 tumors in the nanocarbon-ferrous sulfate composite system groups prepared through two methods respectively.
Figure 41:
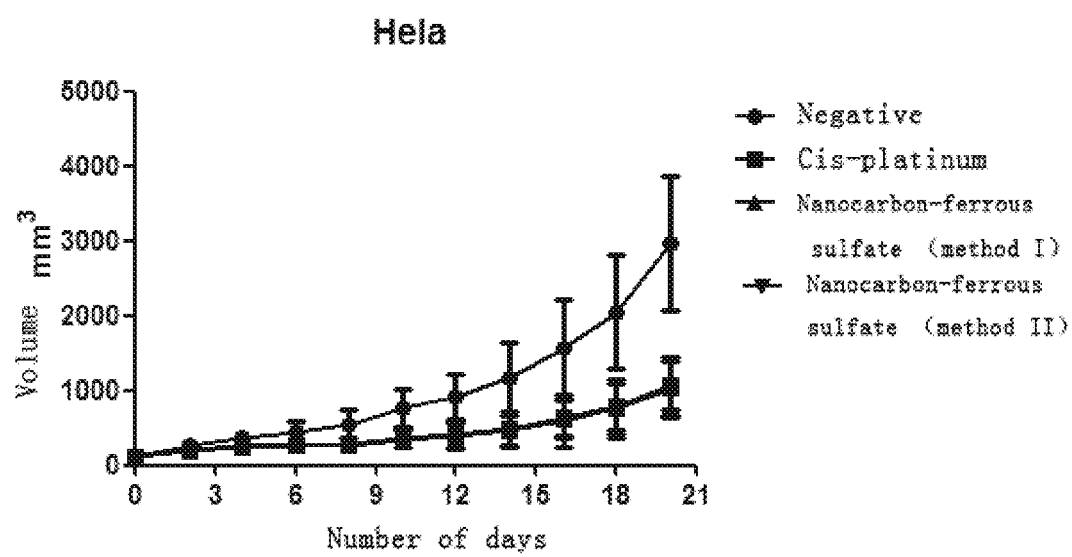
FIG. 41 is a diagram showing the growth and volume of the Hela tumors in the nanocarbon-ferrous sulfate composite system groups prepared through two methods respectively.
Figure 42:
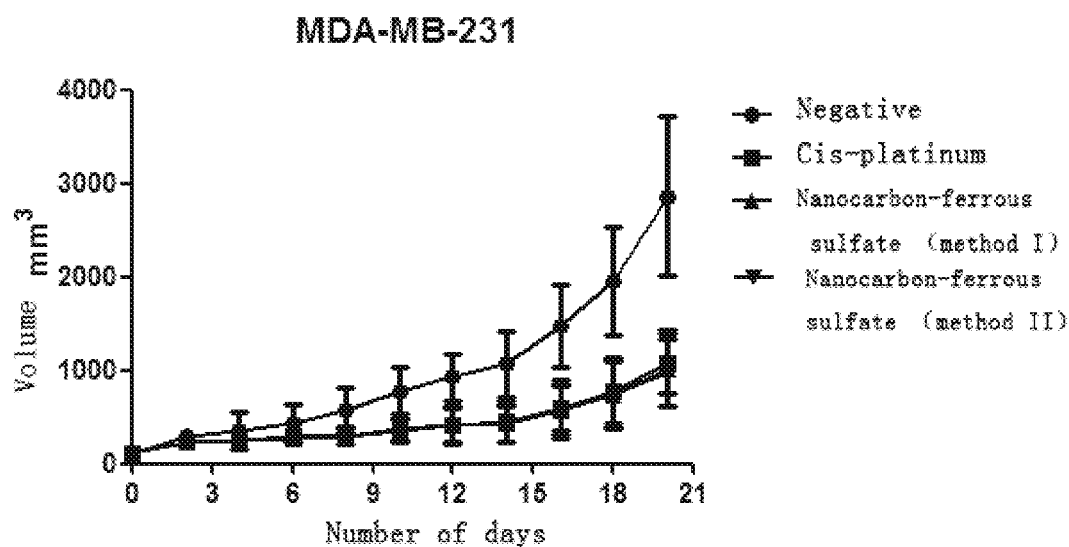
FIG. 42 is a diagram showing the growth and volume of the MDA-MB-231 tumors in the nanocarbon-ferrous sulfate composite system groups prepared through two methods respectively.

Since there are two methods to prepare the nanocarbon-ferrous sulfate composite system, therapeutic effects of nanocarbon-ferrous sulfate composite systems, which are prepared through the two methods respectively, on H22 liver cancer cells, Hela cervical cancer cells and MDA-MB-231 breast cancer cells are compared and the results are shown in FIGS. 40-42. The nanocarbon-ferrous sulfate composite systems prepared through the two methods respectively have a better inhibition effect on all three types of cancer cells and there is no significant difference therebetween.

TABLE 22

Inhibition effects of nanocarbon-ferrous sulfate at different mass ratios on H22 tumor growth

| | Mass Ratio | | | | | | | | |
|---|---|---|---|---|---|---|---|---|---|
| | 2:1 | 5:1 | 6:1 | 12:1 | 18:1 | 24:1 | 30:1 | 35:1 | 40:1 |
| Tumor Inhibition Ratio (%) | 80.93 | 81.73 | 80.06 | 76.17 | 73.10 | 68.13 | 52.14 | 31.23 | 26.87 |

By simultaneously examining the inhibition effects of mixtures of nanocarbon with ferrous sulfate, ferrous gluconate, ammonium ferric citrate and iron sucrose respectively on lymph node metastasis of various cancer cells, the results show that in the four iron preparations, the nanocarbon-ferrous sulfate mixture has the strongest inhibition effect, the weight of metastatic lymph nodes and the metastasis ratio are obviously reduced, and the inhibition effects of the mixture on 9 types of tumor cells including H22, A549, HCT, Hela, MDA-MB-231, SGC-7901, SKOV3, SMMC-7721 and TPC-1 in animals and detailed animal experiment comparison results are shown in table 23. The nanocarbon, ferrous sulfate, ferrous gluconate, ammonium ferric citrate and iron sucrose alone do not have an inhibition effect on the metastatic lymph nodes; nanocarbon-ferrous gluconate and nanocarbon-ammonium ferric citrate also do not have an inhibition effect on the lymph nodes, nanocarbon-iron sucrose has an inhibition effect on lymph node metastasis of H22 and TPC-1 ($P<0.05$), but nanocarbon-ferrous sulfate has an inhibition effect on metastasis of 9 types of lymph nodes.

TABLE 23

The weight of lymph nodes after nanocarbon-iron acts on metastatic lymph nodes of various cancer cells

| | Weight of Lymph Node (mg) | | | | |
|---|---|---|---|---|---|
| Group | H22 | SKOV3 | SGC-7901 | SMMC-7721 | Hela |
| Negative | 53.38 ± 13.21 | 33.66 ± 4.21 | 47.13 ± 18.46 | 55.00 ± 18.41 | 30.14 ± 7.69 |
| Nanocarbon | 58.41 ± 15.97 | 32.53 ±13.79 | 45.97 ± 13.29 | 52.45 ± 6.64 | 33.98 ± 15.74 |
| Ferrous Sulfate | 44.27 ± 20.69 | 35.62 ± 6.94 | 50.12 ± 20.94 | 50.19 ± 18.73 | 29.48 ± 6.46 |
| Nanocarbon-Ferrous Sulfate | 14.67 ± 12.08** | 13.68 ± 7.9** | 18.34 ± 9.76** | 20.65 ± 11.29** | 12.94 ± 8.93** |
| Ferrous Gluconate | 57.19 ± 15.92 | 33.57 ± 5.94 | 52.14 ± 17.43 | 58.97 ± 19.63 | 32.14 ± 21.36 |
| Nanocarbon-Ferrous Gluconate | 50.31 ± 26.74 | 37.42 ± 12.11 | 49.68 ± 12.94 | 51.23 ± 27.91 | 27.61 ± 20.18 |
| Ammonium Ferric Citrate | 53.94 ± 11.58 | 32.98 ± 6.42 | 43.69 ± 8.97 | 56.98 ± 17.59 | 30.94 ± 10.68 |
| Nanocarbon-Ammonium Ferric Citrate | 47.11 ± 14.84 | 34.25 ± 9.16 | 40.19 ± 13.75 | 53.06 ± 23.27 | 31.28 ± 14.75 |
| Iron Sucrose | 62.26 ± 24.06 | 37.94 ± 6.78 | 50.98 ± 21.69 | 49.68 ± 18.67 | 34.26 ± 14.25 |
| Nanocarbon-Iron Sucrose | 39.29 ± 12.10* | 35.17 ± 8.94 | 40.67 ± 18.37 | 54.68 ± 13.24 | 28.94 ± 13.68 |

| | Weight of Lymph Node (mg) | | | |
|---|---|---|---|---|
| Group | MDA-MB-231 | TPC-1 | HCT116 | A549 |
| Negative | 43.15 ± 12.39 | 38.49 ± 4.81 | 52.17 ± 9.02 | 42.24 ± 10.95 |
| Nanocarbon | 47.98 ± 18.92 | 36.19 ± 10.64 | 49.15 ± 17.67 | 40.19 ± 12.68 |
| Ferrous Sulfate | 40.18 ± 11.14 | 35.71 ± 13.45 | 48.12 ± 10.58 | 44.97 ± 16.53 |
| Nanocarbon-Ferrous Sulfate | 17.68 ± 10.36** | 28.91 ± 4.56* | 19.26 ± 6.05** | 15.62 ± 10.75** |

TABLE 23-continued

The weight of lymph nodes after nanocarbon-iron acts on metastatic lymph nodes of various cancer cells

| | | | | |
|---|---|---|---|---|
| Ferrous Gluconate | 40.19 ± 20.69 | 40.16 ± 9.03 | 55.18 ± 20.12 | 47.58 ± 20.34 |
| Nanocarbon-Ferrous Gluconate | 44.18 ± 13.45 | 42.98 ± 14.39 | 50.16 ± 14.54 | 41.36 ± 13.78 |
| Ammonium Ferric Citrate | 46.97 ± 10.36 | 41.97 ± 20.12 | 49.57 ± 20.67 | 45.67 ± 10.68 |
| Nanocarbon-Ammonium Ferric Citrate | 42.19 ± 20.36 | 39.47 ± 7.56 | 54.25 ± 13.49 | 35.97 ± 16.48 |
| Iron Sucrose | 45.69 ± 16.45 | 35.68 ± 10.38 | 53.47 ± 10.87 | 43.35 ± 11.68 |
| Nanocarbon-Iron Sucrose | 40.39 ± 15.67 | 30.19± 8.03* | 45.87 ± 21.89 | 38.97 ± 12.43 |

Notes: the symbol "*" denotes P<0.05 in comparison with the negative group; and the symbol "**" denotes P<0.01 in comparison with the negative group.

Figure 3:
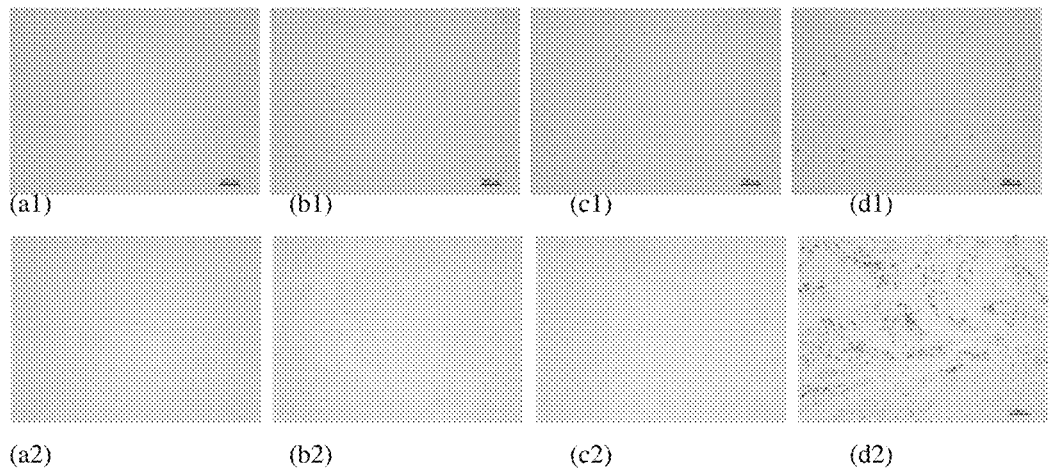

In the cell experiments, there is no stained ferric ion in the negative group (a1), nanocarbon group (b1) and ferrous sulfate group (c1), and there are more stained ferric ions visible in the nanocarbon-ferrous sulfate group (d1). In the animal tumors, no ferric ion can be observed in the negative group (a2) and nanocarbon group (b2); few ferric ions can be observed in the ferrous sulfate group (c1); and a large number of ferric ions can be observed in the nanocarbon-ferrous sulfate group (d2). The results are shown in FIG. 3. This indicates that the nanocarbon-iron composite system can effectively transfer iron into the cells to increase the concentration of iron in the cells.

Figure 44:
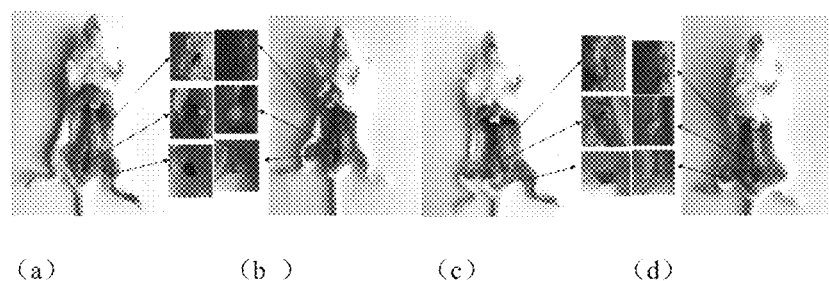
FIG. 44a is a diagram showing a tracing effect of nanocarbon on mouse lymph nodes.
FIG. 44b is a diagram showing a tracing effect of carbon nanotubes on mouse lymph nodes.
FIG. 44c is a diagram showing a tracing effect of the nanocarbon-ferrous sulfate composite system group on mouse lymph nodes.
FIG. 44d is a diagram showing a tracing effect of the carbon nanotubes-ferrous sulfate composite system group on mouse lymph nodes.

In order to screen a proper carrier, we compare the tracing effect of nanocarbon-ferrous sulfate and carbon nanotube-ferrous sulfate on mouse lymph nodes. In the tracing results of mouse lymph nodes, the nanocarbon and nanocarbon-ferrous sulfate have better tracing effects, while the carbon nanotube and carbon nanotube-ferrous sulfate have a poor tracing effect. The results are shown in FIG. 44 and the scoring results are shown in table 24. The nanocarbon has an excellent tracing effect that lymph nodes at three sites are completely stained with black; and the nanocarbon-ferrous sulfate also has a better tracing effect that lymph nodes at three sites are completely stained with black, but the black-stained lymph nodes are less black than that of nanocarbon. The carbon nanotube has a poor tracing effect that only the popliteal lymph node is partially stained with black, and does not have tracing effect on the common iliac lymph node and paraaortic lymph node, and the carbon nanotube-ferrous sulfate does not have a tracing effect. Therefore, the nanocarbon is selected as the carrier.

TABLE 24

Tracing and scoring results of nanocarbon, carbon nanotubes, nanocarbon-ferrous sulfate and carbon nanotube-ferrous sulfate

| | Lymph Node Score | | |
|---|---|---|---|
| Sample Name | Popliteal Lymph Node | Common Iliac Lymph Node | Paraaortic Lymph Node |
| Nanocarbon | 1 | 1 | 1 |
| Carbon Nanotubes | 0.5 | 0 | 0 |
| Nanocarbon-Ferrous Sulfate | 1 | 1 | 1 |
| Carbon Nanotube-Ferrous Sulfate | 0 | 0 | 0 |

It should be noted that the above description only aims to illustrate the technical solution of the present invention without limitation. Although the present invention is described in detail with reference to the above embodiments, it should be understood by an ordinary person skilled in the art that modifications or equivalent replacements may be made to the present invention, and any modifications or partial replacements made without departing from the spirit and scope of the present invention should be comprised within the protection scope of the present invention.

What is claimed is:

1. A nanocarbon-iron composite system being a composite structure which is formed by acid-treated nanocarbon serving as a carrier, and the nanocarbon contains a certain amount of carboxyl on the surface, and ferrous ions and/or ferric ions in an iron salt, wherein the carboxyl has a content range of 0.03 mmol/g-0.08 mmol/g, wherein the composite system has a particle size of 90-300 nm.

2. The composite system according to claim 1, wherein the ferrous ions and/or ferric ions in the iron salt have a concentration of 1.36-13.6 mg/mL.

3. The composite system according to claim 2, wherein the iron salt is selected from any one or more of ferrous sulfate, ferric sulfate, ferrous chloride, ferric chloride, ferrous gluconate, iron sucrose, ammonium ferric citrate, ferrous succinate, iron sorbitol and ferrous fumarate.

4. The composite system according to claim 3, wherein the mass ratio of the nanocarbon to an iron element in the iron salt is 40:1-3:1.

5. The nanocarbon-iron composite system according to claim 2, wherein the composite system has a pH of 3.0-6.0.

6. The composite system according to claim 2, wherein the nanocarbon has a carbon content of 86-98%, a hydrogen content of 0.5-2.5%, and an oxygen content of 1.0-10.0%.

7. The composite system according to claim 2, further comprising sodium citrate, wherein the mass ratio of the sodium citrate to the iron element in the iron salt is 0.1-3.

8. The nanocarbon-iron composite system according to claim 1, wherein the composite system has a pH of 3.0-6.0.

9. The composite system according to claim 1, wherein the mass ratio of the nanocarbon to an iron element in the iron salt is 40:1-3:1.

10. The composite system according to claim 1, wherein the nanocarbon has a carbon content of 86-98%, a hydrogen content of 0.5-2.5%, and an oxygen content of 1.0-10.0%.

11. The composite system according to claim 10, wherein the nanocarbon comprises at least one or more of carbon nanoparticles, carbon nanotubes, carbon quantum dots, graphene, fullerene, carbon nanorods, carbon nanofibres and nano-carbon-black $C_{40}$.

12. The composite system according to claim 11, wherein the nanocarbon has a carboxyl content of 0.01-2.0 mmol/g.

13. The composite system according to claim 1, wherein the nanocarbon and the iron salt form a composite structure by a combination of electrostatic interaction, complexation and the Van der Waals force.

14. The composite system according to claim 1, further comprising sodium citrate, wherein the mass ratio of the sodium citrate to the iron element in the iron salt is 0.1-3.

15. The composite system according to claim 14, wherein the sodium citrate forms a complex with ferrous ions; and/or the sodium citrate forms a complex with iron ions.

16. The composite system according to claim 1, further comprising a suspending agent, wherein the suspending agent is selected from one or more of methylcellulose, sodium carboxymethylcellulose, hydroxypropyl cellulose, polyvinylpyrrolidone $K_{30}$ and glucan.

17. The composite system according to claim 16, wherein the suspending agent has a concentration of 10-40 mg/ml.

18. The composite system according to claim 1, wherein the nanocarbon-iron composite system is utilized in preparation of a drug for treating liver cancer, lung cancer, stomach cancer, colon cancer, breast cancer, cervical cancer, thyroid cancer or ovarian cancer.

19. A suspension for injection, comprising a nanocarbon-iron composite system being a composite structure which is formed by acid-treated nanocarbon serving as a carrier, and the nanocarbon contains a certain amount of carboxyl on the surface, and ferrous ions and/or ferric ions in an iron salt, wherein the carboxyl has a content range of 0.03 mmol/g-0.08 mmol/g, wherein the composite system has a particle size of 90-300 nm, wherein the nanocarbon-iron composite system is dispersed uniformly and stably in a mixed solution containing polyvinylpyrrolidone K30 and sodium citrate; in the composite system, the ferrous irons or/and ferric ions have a concentration of 1.36-13.6 mg/mL.

* * * * *